(12) United States Patent
Inagaki et al.

(10) Patent No.: US 10,516,115 B2
(45) Date of Patent: Dec. 24, 2019

(54) ORGANIC COMPOUND, METHOD FOR PREPARING SAME, ORGANIC SEMICONDUCTOR MATERIAL CONTAINING SAME, AND ORGANIC TRANSISTOR CONTAINING SAME

(71) Applicant: DIC Corporation, Tokyo (JP)

(72) Inventors: Sho Inagaki, Chiba (JP); Ryo Minakuchi, Chiba (JP); Hideki Etori, Chiba (JP); Aya Ishizuka, Chiba (JP)

(73) Assignee: DIC CORPORATION, Tokyo (JP)

(*) Notice: Subject to any disclaimer, the term of this patent is extended or adjusted under 35 U.S.C. 154(b) by 0 days.

(21) Appl. No.: 15/755,395

(22) PCT Filed: Jul. 21, 2016

(86) PCT No.: PCT/JP2016/071379
§ 371 (c)(1),
(2) Date: Feb. 26, 2018

(87) PCT Pub. No.: WO2017/038286
PCT Pub. Date: Mar. 9, 2017

(65) Prior Publication Data
US 2018/0248131 A1 Aug. 30, 2018

(30) Foreign Application Priority Data
Aug. 28, 2015 (JP) ................. 2015-169100

(51) Int. Cl.
*C07D 333/50* (2006.01)
*H01L 51/00* (2006.01)
*C09D 11/52* (2014.01)
*C09D 11/30* (2014.01)
*H01L 51/05* (2006.01)

(52) U.S. Cl.
CPC ........ *H01L 51/0074* (2013.01); *C07D 333/50* (2013.01); *C09D 11/30* (2013.01); *C09D 11/52* (2013.01); *H01L 51/0068* (2013.01); *H01L 51/0004* (2013.01); *H01L 51/0005* (2013.01); *H01L 51/0558* (2013.01)

(58) Field of Classification Search
CPC .................................................. H01L 51/0074
USPC ......................................................... 549/41
See application file for complete search history.

(56) References Cited

U.S. PATENT DOCUMENTS

| | | | | |
|---|---|---|---|---|
| 9,481,662 B2* | 11/2016 | Fenical | ............... | G01N 33/5011 |
| 2012/0141939 A1 | 6/2012 | Thackeray et al. | | |
| 2015/0014673 A1* | 1/2015 | Takeya | ................. | C07D 333/50 257/40 |
| 2015/0148314 A1 | 5/2015 | Fenical et al. | | |
| 2015/0372241 A1 | 12/2015 | Park et al. | | |
| 2016/0013425 A1 | 1/2016 | Takeya et al. | | |
| 2016/0351817 A1* | 12/2016 | Kim | ..................... | H01L 51/0052 |
| 2017/0098786 A1* | 4/2017 | Kitamura | ............ | H01L 51/0074 |

FOREIGN PATENT DOCUMENTS

| | | | |
|---|---|---|---|
| JP | 2007-197400 A | | 8/2007 |
| JP | 2010/045281 A | * | 2/2010 |
| JP | 2012-136511 A | | 7/2012 |
| KR | 10-2012-0104067 A | | 9/2012 |
| KR | 10-2013-0075982 A | | 7/2013 |
| WO | 2010/058692 A1 | | 5/2010 |
| WO | 2012/115236 A1 | | 8/2012 |
| WO | 2012/121393 A1 | | 9/2012 |
| WO | 2013/125599 A1 | | 8/2013 |
| WO | 2014/018919 A1 | | 1/2014 |
| WO | 2014/038708 A1 | | 3/2014 |
| WO | 2014/136827 A1 | | 9/2014 |
| WO | 2015/137304 A1 | | 9/2015 |
| WO | WO 2015/137304 A1 | * | 9/2015 |

OTHER PUBLICATIONS

Li et al., Sepu (2011), 29(1), pp. 63-69.*
Trzoss et al., Proceedings Nat. Acad. Sc. USA (2014), 111(41), pp. 14687-14692.*
King, Med. Chem., Principle and Practice (1994), pp. 206-208.*
Minemawari, H. et al., "Inkjet printing of single-crystal films," Nature, Jul. 21, 2011, vol. 475, pp. 364-367.

(Continued)

*Primary Examiner* — Taofiq A Solola
(74) *Attorney, Agent, or Firm* — McDermott Will & Emery LLP

(57) ABSTRACT

Provided are a compound which is excellent in solubility in a solvent and easily provides a film exhibiting high mobility without complicated processes, an organic semiconductor material using the same, and an organic semiconductor ink which enables easy fabrication of an organic transistor composed of a practical configuration. The problems are solved by a method of producing a dinaphthothiophene derivative, the method including the following steps (I) and (II): (I) a first step of subjecting a naphthol derivative represented by General Formula (A) and a naphthalene thiol derivative represented by General Formula (B) to dehydration condensation in the presence of acid to produce a sulfide derivative represented by General formula (C); and (II) a second step of performing dehydrogenation reaction of the sulfide derivative (C) in the presence of a transition metal salt or a transition metal complex to produce a dinaphthothiophene derivative (D).

9 Claims, 1 Drawing Sheet

(56) References Cited

OTHER PUBLICATIONS

Search Report issued in corresponding International Patent Application No. PCT/JP2016/071379, dated Sep. 27, 2016, with English language translation.
Okamoto, Toshihiro et al., "V-Shaped Organic Semiconductors With Solution Processability, High Mobility, and High Thermal Durability," Advanced Materials, 2013, vol. 25, pp. 6392-6397.
Tedjamulia, M. L. et al., "The Synthesis of Dinaphthothiophenes," Journal of Heterocyclic Chemistry, 1983, vol. 20, pp. 1143-1148.
Che, R. et al., "Synthesis of Dibenzothiophenes by Pd-Catalyzed Dual C—H Activation from Diaryl Sulfides," Chemistry A European Journal, 2014, vol. 20, pp. 7258-7261.
Qiao, Z. et al., "CO2-promoted oxidative cross-coupling reaction for C—S bond formation via masked strategy in an odourless way," Chemical Communications, Jun. 28, 2015, vol. 51, No. 51, pp. 10295-10298.
Trosien, S. et al., "Versatile Oxidative Approach to Carbazoles and Related Compounds Using MoCl5," Organic Letters, 2014, vol. 16, pp. 402-405.
Sadorn, K. et al., "An efficient synthesis of dinaphthothiophene derivatives," Tetrahedron Letters, 2008, vol. 49, pp. 4519-4521.
Wu, D. et al., "Oxygen- and Sulfur-Containing Positively Charged Polycyclic Aromatic Hydrocarbons," Organic Letters, 2009, vol. 11, No. 24, pp. 5686-5689.

* cited by examiner

ORGANIC COMPOUND, METHOD FOR PREPARING SAME, ORGANIC SEMICONDUCTOR MATERIAL CONTAINING SAME, AND ORGANIC TRANSISTOR CONTAINING SAME

CROSS REFERENCE

This application is the U.S. National Phase under 35 U.S.C. § 371 of International Application No. PCT/JP2016/071379, filed on Jul. 21, 2016, which claims the benefit of Japanese Application No. 2015-169100, filed on Aug. 28, 2015, the entire contents of each are hereby incorporated by reference.

TECHNICAL FIELD

The present invention relates to a dinaphthothiophene derivative, a method of preparing the same, an organic semiconductor material containing the same, an organic semiconductor ink containing the same, and an organic transistor containing the same.

BACKGROUND ART

In the related art, a thin-film transistor (TFT) in which amorphous silicon or polycrystalline silicon is used as a material has been widely used as a switching element for a liquid crystal display device, an organic EL display device, and the like. However, a CVD apparatus used for producing a transistor using the silicon materials is expensive and thus, producing of a large transistor integrated circuit leads to an increase in producing cost. In addition, the silicon material is formed into a film at high temperature, and therefore, due to a problem of heat resistance, cannot be applied to a next generation flexible display device in which a plastic substrate is supposed to be used. In order to solve this problem, an organic transistor in which an organic semiconductor material is used as a channel (semiconductor layer) instead of the silicon semiconductor material has been proposed.

Since it is possible to form a film at low temperature by using the organic semiconductor material as an ink, a large-scale production facility is not required. In addition, the organic semiconductor material can be applied to a plastic substrate with poor heat resistance and has been expected to be applied to flexible electronics.

Such an organic semiconductor material had a problem in that, since semiconductor properties (mobility) are poor as compared with the silicon semiconductor materials, a response speed of the transistor is slow and thereby it is difficult to put it into practical use; however, in recent years, materials, the mobility of which exceeds that of amorphous silicon, have been developed.

For example, PTL 1 discloses that a compound having a dinaphtho[2,3-b:2',3'-f]thieno[3,2-b]thiophene skeleton exhibits mobility of 4.0 $cm^2/Vs$ in a vacuum evaporated film, PTLs 2 and 3 disclose that a dinaphtho[2,3-b:2',3'-d]thiophene (hereinafter, abbreviated as dinaphthothiophene) derivative exhibits a high mobility of 11 $cm^2/Vs$ in a single crystal thin film formed by an edge casting method, NPL 1 discloses that 2,7-dioctyl[1]benzothieno[3,2-b][1]benzothiophene exhibits a high mobility of 30 $cm^2/Vs$ in a single crystal film prepared by a double ink jet method while its properties have large variation, PTL 4 discloses that a phenyl substituted naphthodichalcogen compound exhibits a mobility of 0.7 $cm^2/Vs$, and PTLs 5 and 6 disclose that a compound exhibiting a highly ordered liquid crystal phase shows a mobility of 5.7 $cm^2/Vs$ in a thin film formed via a highly ordered liquid crystal phase. As such, the organic semiconductor materials exhibiting the semiconductor properties where the mobility thereof exceeds that of amorphous silicon (0.5 $cm^2/Vs$) have been reported one after another.

Although the mobility of the organic semiconductors has been increased in this way, it has not yet been put to practical use. The reason is that the mobility as disclosed above is evaluated by using a semiconductor layer composed of a film prepared by a film-forming method which gives a homogeneous bulk such as a single crystal film prepared by an edge casting method or a double ink jet method, a thin film prepared by a vacuum deposition method and a thin film prepared by a spin coating method, and in the case of using the semiconductor layer made of a polycrystalline film which is prepared by dropping (drop-casting) an ink droplet and then drying it, that is, a practical printing method such as an ink jet method and a nozzle printing method, the properties are deteriorated.

CITATION LIST

Patent Literature

[PTL 1] WO 2012/115236
[PTL 2] WO 2013/125599
[PTL 3] JP-A-2007-197400
[PTL 4] WO 2010/058692
[PTL 5] WO 2012/121393
[PTL 6] WO 2014/038708

Non Patent Literature

[NPL 1] Nature, 2011, vol. 475, p. 364

SUMMARY OF INVENTION

Technical Problem

The organic semiconductor material in the related art has poor solubility in a solvent, and thus it is difficult to prepare an ink. Accordingly, there was a problem in film formation by a wet process which is required for establishing a printing process. In addition, even for a material having solvent solubility, there are some problems in preparation of a homogeneous film, because disorder of molecular orientation, partial crystallization, and the like take place during a wet process. Thus, in order to obtain high mobility, a film-formation method which is difficult to put into practical use and/or a complicated post deposition process such as an annealing treatment were required.

In this regard, an object of the present invention is to provide a compound which is excellent in solubility in a solvent and easily provides a film exhibiting high mobility without complicated processes, that is, a film exhibiting high mobility only by drop-casting ink droplets and then drying them, an organic semiconductor material using the same, and an organic semiconductor ink which enables easy fabrication of an organic transistor composed of a practical configuration.

Solution to Problem

In order to achieve the above-mentioned object, the present inventors have repeatedly conducted intensive studies, found that dinaphthothiophene having a specific substituent-position structure has excellent solubility in a solvent, therefore has suitability as an organic semiconductor ink, and can provide an organic semiconductor film having high mobility even by not a complicated method but a simple and practical wet film formation method, that is, a method of drop-casting and drying of ink droplets, and thereby completed the present invention.

That is, the present invention is configured as follows.

1. A preparing method of a dinaphthothiophene derivative represented by General Formula (D), the method including the following steps (I) and (II):

(I) a first step of subjecting a naphthol derivative represented by General Formula (A) and a naphthalene thiol derivative represented by General Formula (B) to dehydration condensation in the presence of acid to produce a sulfide derivative represented by General formula (C); and (II) a second step of performing dehydrogenation reaction of the sulfide derivative (C) in the presence of a transition metal salt or a transition metal complex to produce a dinaphthothiophene derivative represented by General Formula (D).

[Chem. 1]

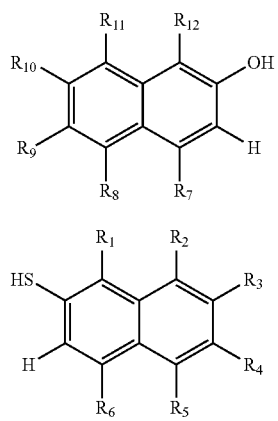

(A)

(B)

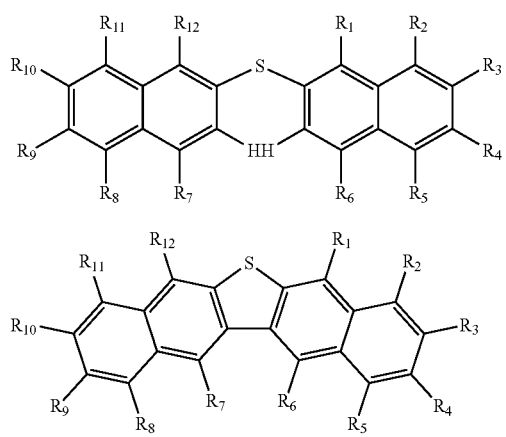

(C)

(D)

In the formulae, $R_1$ to $R_{12}$ each represent a hydrogen atom or an arbitrary substituent.

2. The preparing method described in the item 1, wherein $R_1$ to $R_{12}$ each are a hydrogen atom; an acyclic or cyclic alkyl group having 1 to 20 carbon atoms wherein at least one hydrogen atom in the alkyl group may be substituted with an aromatic group, a halogeno group or a nitrile group, and at least one —$CH_2$— in the alkyl group may be replaced by —O—, —R'C=CR'—, —CO—, —OCO—, —COO—, —S—, —$SO_2$—, —SO—, —NH—, —NR'— or —C≡— provided that, with respect to each of an oxygen atom, a sulfur atom and a nitrogen atom, the same atoms are not directly bonded to each other, wherein R' represents an acyclic or cyclic alkyl group having 1 to 20 carbon atoms; a halogeno group; an aromatic group wherein the aromatic group may be substituted with an acyclic or cyclic alkyl group having 1 to 20 carbon atoms, a halogeno group, an aromatic group or a nitrile group, wherein at least one hydrogen atom in the alkyl group may be substituted with an aromatic group, a halogeno group or a nitrile group, and at least one —$CH_2$— in the alkyl group may be replaced by —O—, —CR"=CR"—, —CO—, —OCO—, —COO—, —S—, —$SO_2$—, —SO—, —NH—, —NR"— or —C≡— provided that, with respect to each of an oxygen atom, a sulfur atom and a nitrogen atom, the same atoms are not directly bonded to each other, wherein R" represents an acyclic or cyclic alkyl group having 1 to 20 carbon atoms; a nitro group; or a nitrile group.

3. The preparing method described in the item 1 or 2, wherein $R_1$ and $R_{12}$ are the same as or different from each other, $R_2$ and $R_{11}$ are the same as or different from each other, $R_3$ and $R_{10}$ are the same as or different from each other, $R_4$ and $R_9$ are the same as or different from each other, $R_5$ and $R_8$ are the same as or different from each other, and $R_6$ and $R_7$ are the same as or different from each other provided that, in terms of at least one combination of the six combinations of $R_1$ and $R_{12}$, $R_2$ and $R_{11}$, $R_3$ and $R_{10}$, $R_4$ and $R_9$, $R_5$ and $R_8$, and $R_6$ and $R_7$, the two substituents which constitute the combination are different from each other.

4. A dinaphthothiophene derivative represented by General Formula (E) excluding a compound (E-a), a compound (E-b), a compound (E-c), a compound (E-d), a compound (E-e), a compound (E-f), a compound (E-g), a compound (E-h), a compound (E-i), a compound (E-j), a compound (E-k) and a compound (E-L).

[Chem. 2]

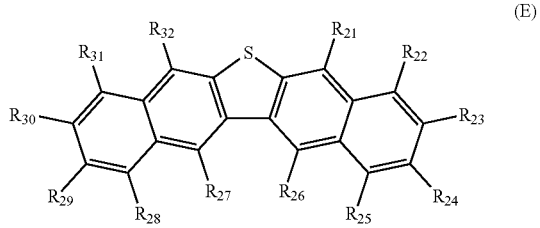

(E)

In the formula, $R_{21}$ to $R_{32}$ each are a hydrogen atom or an arbitrary substituent, $R_{21}$ and $R_{32}$ are the same as or different from each other, $R_{22}$ and $R_{31}$ are the same as or different from each other, $R_{23}$ and $R_{30}$ are the same as or different from each other, $R_{24}$ and $R_{29}$ are the same as or different from each other, $R_{25}$ and $R_{28}$ are the same as or different from each other, and $R_{26}$ and $R_{27}$ are the same as or different from each other, provided that in terms of at least one combination of the six combinations of $R_{21}$ and $R_{32}$, $R_{22}$ and $R_{31}$, $R_{23}$ and $R_{30}$, $R_{24}$ and $R_{29}$, $R_{25}$ and $R_{28}$, and $R_{26}$ and $R_{27}$, the two substituents which constitute the combination are different from each other.

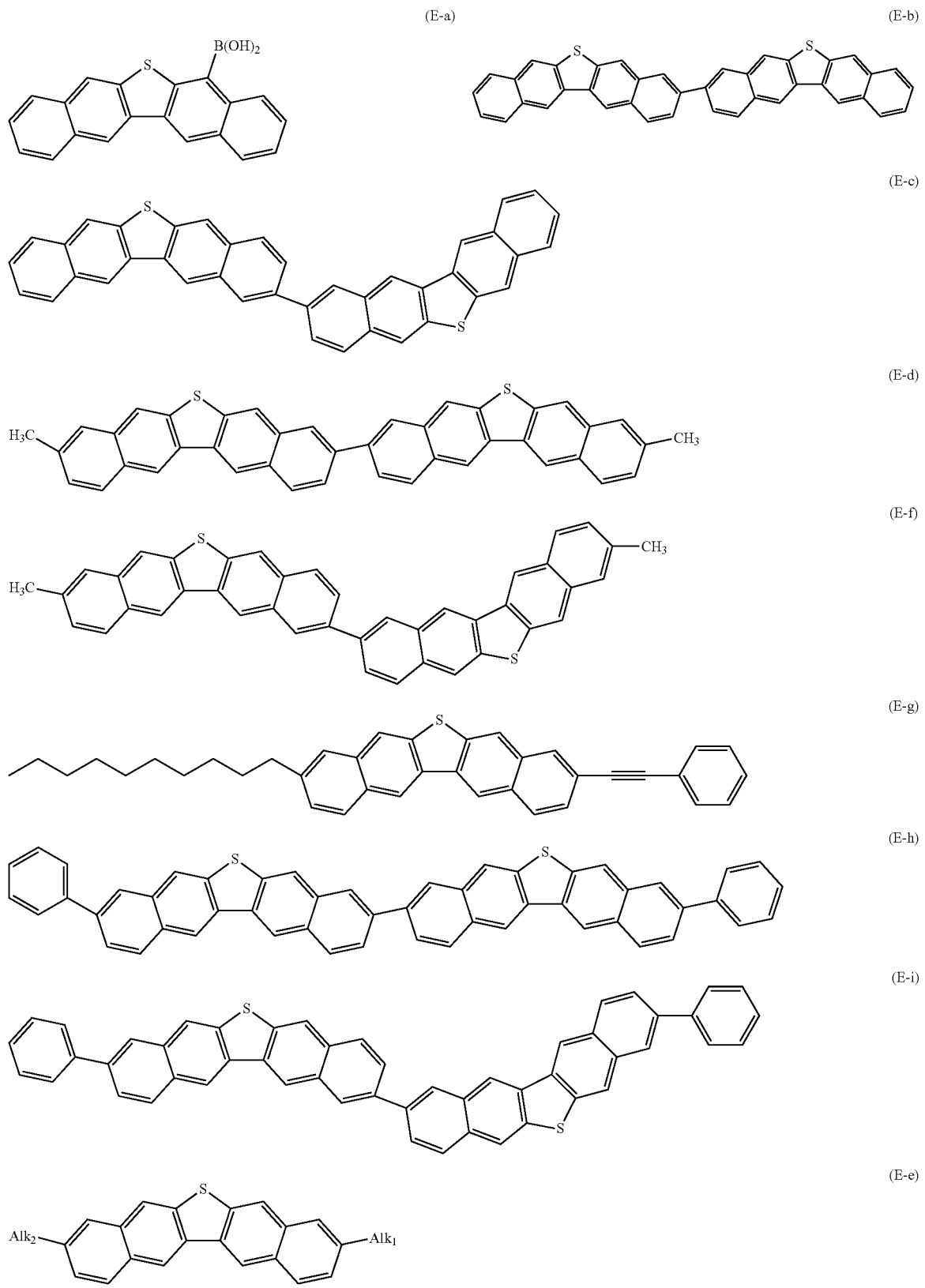

In the formula, Alk1 and Alk2 represent a linear alkyl group having 1 to 30 carbon atoms.

[Chem. 4]

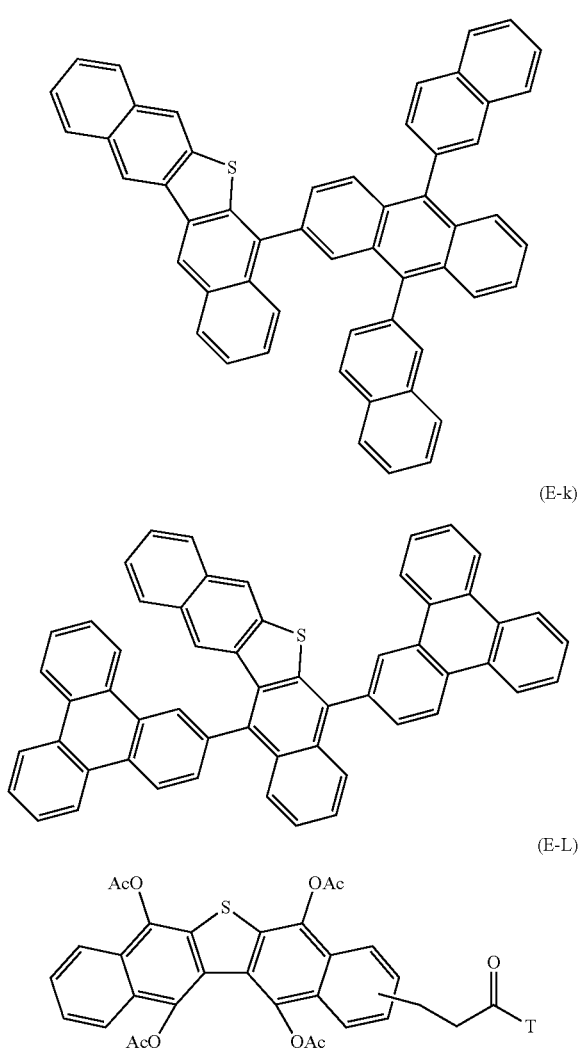

In the formula, Ac represents an acetyl group and T represents an arbitrary substituent.

5. The dinaphthothiophene derivative described in the item 4, wherein $R_{21}$ to $R_{32}$ each are a hydrogen atom; an acyclic or cyclic alkyl group having 1 to 20 carbon atoms wherein at least one hydrogen atom in the alkyl group may be substituted with an aromatic group, a halogeno group or a nitrile group, and at least one —CH$_2$— in the alkyl group may be replaced by —O—, —R'C═CR'—, —CO—, —OCO—, —COO—, —S—, —SO$_2$—, —SO—, —NH—, —NR'— or —C≡— provided that, with respect to each of an oxygen atom, a sulfur atom and a nitrogen atom, the same atoms are not directly bonded to each other, wherein R' represents an acyclic or cyclic alkyl group having 1 to 20 carbon atoms; a halogeno group; an aromatic group wherein the aromatic group may be substituted with an acyclic or cyclic alkyl group having 1 to 20 carbon atoms, a halogeno group, an aromatic group or a nitrile group, wherein at least one hydrogen atom in the alkyl group may be substituted with an aromatic group, a halogeno group or a nitrile group, and at least one —CH$_2$— in the alkyl group may be replaced by —O—, —CR''═CR''—, —CO—, —OCO—, —COO—, —S—, —SO$_2$—, —SO—, —NH—, —NR''— or —C≡— provided that, with respect to each of an oxygen atom, a sulfur atom and a nitrogen atom, the same atoms are not directly bonded to each other, wherein R'' represents an acyclic or cyclic alkyl group having 1 to 20 carbon atoms; a nitro group; or a nitrile group.

6. The dinaphthothiophene derivative described in the item 4 or 5, wherein $R_{21}$ to $R_{32}$ each are a hydrogen atom, a fluorine atom (a fluoro group), an acyclic or cyclic alkyl group having 1 to 20 carbon atoms, Ph-C≡C* wherein Ph represents a phenyl group which may be substituted and * represents a bonding position, or Th-C≡C* wherein Th represents a thienyl group which may be substituted and * represents a bonding position.

7. The dinaphthothiophene derivative described in the items 4 to 6, wherein in terms of at least one combination of the six combinations of $R_{21}$ and $R_{32}$, $R_{22}$ and $R_{31}$, $R_{23}$ and $R_{30}$, $R_{24}$ and $R_{29}$, $R_{25}$ and $R_{28}$, and $R_{26}$ and $R_{27}$, the two substituents which constitute the combination are different from each other, and the two substituents which constitute each of the other combinations are the same as each other and are hydrogen atoms.

8. The dinaphthothiophene derivative described in the items 4 to 6, wherein among the six combinations of $R_{21}$ and $R_{32}$, $R_{22}$ and $R_{31}$, $R_{23}$ and $R_{30}$, $R_{24}$ and $R_{29}$, $R_{25}$ and $R_{28}$, and $R_{26}$ and $R_{27}$, the two substituents which constitute each of the combinations of $R_{21}$ and $R_{32}$, $R_{22}$ and $R_{31}$, $R_{25}$ and $R_{28}$, and $R_{26}$ and $R_{27}$ are the same as each other and are hydrogen atoms, $R_{23}$ and $R_{30}$ are the same as or different from each other, $R_{24}$ and $R_{29}$ are the same as or different from each other, and, in terms of at least one combination of two combinations of $R_{23}$ and $R_{30}$, and $R_{24}$ and $R_{29}$, the two substituents which constitute the combination are different from each other.

9. An organic semiconductor material including the dinaphthothiophene derivative described in any one of the items 4 to 8.

10. An organic semiconductor ink including the organic semiconductor material described in the item 9.

11. An organic semiconductor film including the organic semiconductor material described in the item 9.

12. An organic semiconductor device including the organic semiconductor material described in the item 9.

13. An organic transistor including the organic semiconductor material described in the item 9.

Advantageous Effects of Invention

According to the present invention, it is possible to provide a dinaphthothiophene compound which has a specific substituent-position structure, therefore has excellent solubility in a solvent and contributes to providing an organic semiconductor film with high mobility even by using a simple and practical wet film formation method, that is, a method of only drop-casting ink droplets and then drying them, a method of preparing the dinaphthothiophene compound, an organic semiconductor material containing the compound, an organic semiconductor ink containing the compound, and an organic transistor containing the compound.

DESCRIPTION OF EMBODIMENTS

Method of Preparing Dinaphthothiophene Derivative

Figure 1:
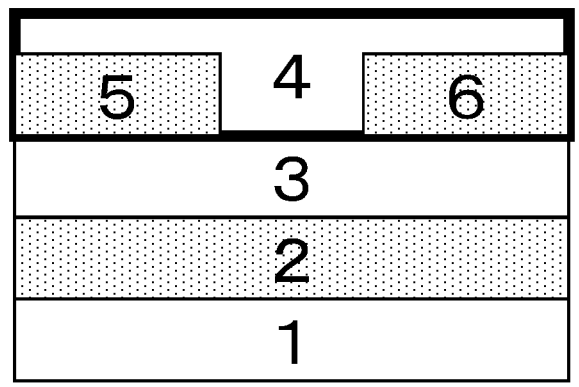
FIG. 1 is a schematic representation of a bottom gate bottom contact type (BC type) transistor.
Figure 2:
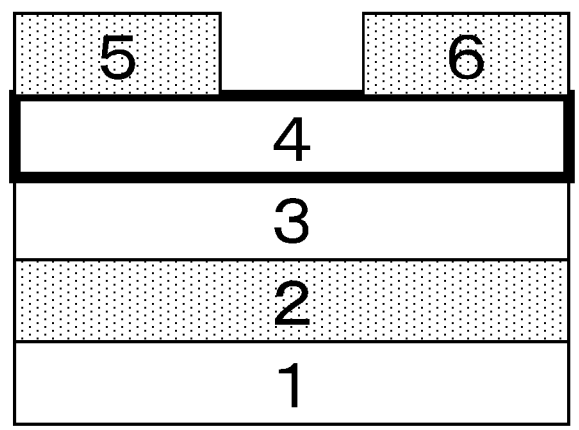
FIG. 2 is a schematic representation of a bottom gate top contact type (TC type) transistor.

A method of preparing a dinaphthothiophene derivative of the present invention will be described.

A scheme of a preparing process of the present invention is as follows.

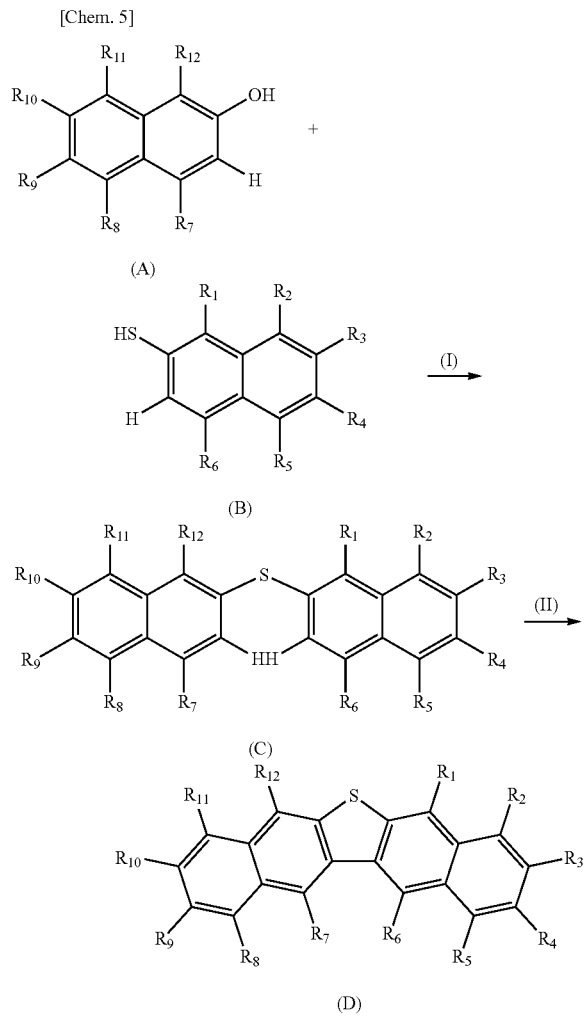

In the respective formulae, $R_1$ to $R_{12}$ each represent a hydrogen atom or an arbitrary substituent.

Here, substituents of $R_1$ to $R_{12}$ of the compounds represented by General Formulae (A), (B), (C) and (D) relating to the preparing method of the present invention may be the same as or different from each other, and an arbitrary substituent, which can not be a reaction active part in the preparing step (I) or (II) described below and is conventionally known as a substituent of the aromatic compound, can be employed. Specific examples thereof include a hydrogen atom including light hydrogen, deuterium hydrogen and tritium hydrogen, an acyclic or cyclic alkyl group having 1 to 20 carbon atoms wherein at least one hydrogen atom in the alkyl group may be substituted with an aromatic group, a halogeno group or a nitrile group, and at least one —$CH_2$— in the alkyl group may be replaced by —O—, —R'C=CR'—, —CO—, —OCO—, —COO—, —S—, —$SO_2$—, —SO—, —NH—, —NR'— or —C≡— provided that, with respect to each of an oxygen atom, a sulfur atom and a nitrogen atom, the same atoms are not directly bonded to each other, wherein R' represents an acyclic or cyclic alkyl group having 1 to 20 carbon atoms; a halogeno group; an aromatic group wherein the aromatic group may be substituted with an acyclic or cyclic alkyl group having 1 to 20 carbon atoms, a halogeno group, an aromatic group or a nitrile group, wherein at least one hydrogen atom in the alkyl group may be substituted with an aromatic group, a halogeno group or a nitrile group and, at least one —$CH_2$— in the alkyl group may be replaced by —O—, —CR"=CR"—, —CO—, —OCO—, —COO—, —S—, —$SO_2$—, —SO—, —NH—, —NR"— or —C≡— provided that, with respect to each of an oxygen atom, a sulfur atom and a nitrogen atom, the same atoms are not directly bonded to each other, wherein R" represents an acyclic or cyclic alkyl group having 1 to 20 carbon atoms; a nitro group; and a nitrile group. Here, the substituents are not limited to these examples. Note that, specific examples of the alkyl group, the halogeno group and the aromatic group include the same substituent as those of the compound (dinaphthothiophene derivative) of the present invention which will be described below.

Regarding the position structure of the substituent, the case where $R_1$ and $R_{12}$ are the same as or different from each other, $R_2$ and $R_{11}$ are the same as or different from each other, $R_3$ and $R_{10}$ are the same as or different from each other, $R_4$ and $R_9$ are the same as or different from each other, $R_5$ and $R_8$ are the same as or different from each other, and $R_6$ and $R_7$ are the same as or different from each other, provided that in terms of at least one combination of six combinations of $R_1$ and $R_{12}$, $R_2$ and $R_{11}$, $R_3$ and $R_{10}$, $R_4$ and $R_9$, $R_5$ and $R_8$, and $R_6$ and $R_7$, the two substituents which constitute the combination are different from each other is preferable; the case which can be achieved with the features of the preparing method described later.

The method of preparing the dinaphthothiophene derivative of the present invention includes (I) a first step of subjecting a naphthol derivative represented by General Formula (A) and a naphthalene thiol derivative represented by General Formula (B) to dehydration condensation in the presence of acid to produce a sulfide derivative represented by General formula (C); and (II) a second step of performing dehydrogenation reaction of the sulfide derivative (C) in the presence of a transition metal salt or a transition metal complex to produce a dinaphthothiophene derivative (D).

Since a conventionally well-known method of preparing a dinaphthothiophene derivative (PTL 2) is performed under the extreme conditions such as the reaction at 300° C., thus kinds of the substituents that can be introduced are limited, and further since the aforementioned method requires multistage synthesis, thus the yield is low. Further, regarding the position structure of the substituent, the aforementioned method, due to the nature of the method, produces only the derivative in which $R_1$ and $R_{12}$ are the same as each other, $R_2$ and $R_{11}$ are the same as each other, $R_3$ and $R_{10}$ are the same as each other, $R_4$ and $R_9$ are the same as each other, $R_5$ and $R_8$ are the same as each other, and $R_6$ and $R_7$ are the same as each other. In contrast, in the present preparing method, since the reaction conditions are mild and the number of steps is small, a number of the substituent group can be used and the yield is high. Further, the present preparing method can produce a dinaphthothiophene derivative in which $R_1$ and $R_{12}$ are the same as or different from each other, $R_2$ and $R_{11}$ are the same as or different from each other, $R_3$ and $R_{10}$ are the same as or different from each other, $R_4$ and $R_9$ are the same as or different from each other, $R_5$ and $R_8$ are the same as or different from each other, $R_6$ and $R_7$ are the same as or different from each other provided that in terms of at least one combination of six combinations of $R_1$ and $R_{12}$, $R_2$ and $R_{11}$, $R_3$ and $R_{10}$, $R_4$ and $R_9$, $R_5$ and $R_8$, and $R_6$ and $R_7$, the two substituents which constitute the combination are different from each other. Such a derivative has suitability as an organic semiconductor ink owing to its excellent solubility in a solvent as described later, and further since its intermolecular force is optimized, can yield an organic semiconductor film with high semiconductor properties (mobility) by using a simple and practical wet film formation method, that is, a method of only drop-casting the ink and then drying it.

Here, a first step will be described.

In the first step, a naphthol derivative (A) and a naphthalene thiol derivative (B) are subjected to dehydration condensation in the presence of acid to thereby prepare a sulfide derivative (C).

The naphthol derivatives (A) are commercially available, and are easy to obtain. In addition, as disclosed in JP-A-61-115039 or the like, the naphthol derivatives (A) can be synthesized in accordance with the method of sulfonating naphthalene, and then melting the naphthalene sulfonic acid with alkali hydroxide.

The naphthalene thiol derivatives (B) are commercially available, and are easy to obtain. In addition, as disclosed in European Journal of Organic Chemistry 833-845 (2010) or the like, the naphthalene thiol derivatives (B) can be synthesized in accordance with the method of condensing naphthol with dimethyl thiocarbamoyl chloride to form 0-thiocarbamate, and then thermally rearranging the 0-thiocarbamate to S-thiocarbamate, and then hydrolyzing the S-thiocarbamate.

A molar ratio of a use amount of the naphthalene thiol derivative (B) with respect to the naphthol derivative (A) is typically in a range of 0.1 to 10, is preferably in a range of 0.2 to 5, and is further preferably in a range of 0.4 to 2.5.

The acid used in the reaction is not particularly limited as long as it shows acidity, and examples thereof include a mineral acid, a sulfonic acid, a salt of metal or metalloid, a complex of metal or metalloid and a solid acid.

Specific examples of the mineral acid include a heteropoly acid such as a hydrochloric acid, a hydrobromic acid, a hydroiodic acid, a perchloric acid, a nitric acid, a sulfuric acid, a phosphoric acid, a boric acid, a polyphosphoric acid, a fluorosulfuric acid, a chlorosulfuric acid and a phosphotungstic acid.

Among the above-described mineral acids, a hydrochloric acid, a nitric acid, a sulfuric acid, a phosphoric acid, a polyphosphoric acid, a fluorosulfuric acid and a chlorosulfuric acid are preferable, and in order to further improve the reactivity, a sulfuric acid, a phosphoric acid, a polyphosphoric acid and a fluorosulfuric acid are further preferable.

Specific examples of the sulfonic acid include an alkyl sulfonic acid such as a methane sulfonic acid, an ethane sulfonic acid, a propane sulfonic acid, a butane sulfonic acid, a pentane sulfonic acid, a hexane sulfonic acid, a heptane sulfonic acid, an octane sulfonic acid, a nonane sulfonic acid and a decane sulfonic acid; a fluorinated alkyl sulfonic acids such as a trifluoromethane sulfonic acid, a perfluoroethane sulfonic acid, a perfluoropropane sulfonic acid, a perfluorobutane sulfonic acid, a perfluoropentane sulfonic acid, a perfluorohexane sulfonic acid, a perfluoroheptane sulfonic acid, a perfluorooctane sulfonic acid, a perfluorononane sulfonic acid and a perfluorodecane sulfonic acid; and an aryl sulfonic acid, which may be substituted with alkyl group, such as a benzene sulfonic acid, a naphthalene sulfonic acid, a pyridine sulfonic acid, a thiophene sulfonic acid, a p-toluene sulfonic acid, a p-styrene sulfonic acid and xylene sulfonic acid.

Among the sulfonic acids, a methane sulfonic acid, an ethane sulfonic acid, a propane sulfonic acid, a butane sulfonic acid, a pentane sulfonic acid, a hexane sulfonic acid, a trifluoromethane sulfonic acid, a perfluoroethane sulfonic acid, a perfluoropropane sulfonic acid, a perfluorobutane sulfonic acid, a perfluoropentane sulfonic acid, a perfluorohexane sulfonic acid, a benzene sulfonic acid, a naphthalene sulfonic acid, a p-toluene sulfonic acid, a p-styrene sulfonic acid and a xylene sulfonic acid are preferable, and in order to further improve the reactivity, a methane sulfonic acid, an ethane sulfonic acid, a trifluoromethane sulfonic acid, a perfluoroethane sulfonic acid, a perfluoropropane sulfonic acid and a perfluorobutane sulfonic acid are further preferable.

The salt of metal or metalloid, and the complex of metal or metalloid are a salt and a complex of elements and acid compounds, or oxygen-bonded elements and acid compounds; examples of the element include Be, B, Al, Si, P, S, Ti, V, Fe, Zn, Ga, Ge, As, Se, Zr, Nb, Mo, Cd, In, Sn, Sb, Te, Yb, Hf, Ta, W, Hg, Tl, Pb, Bi and U, examples of oxygen-bonded elements include PO, SeO and VO, and acid compounds are a mineral acid such as hydrogen fluoride, hydrogen chloride, hydrobromic acid, hydrogen iodide, a perchloric acid, a nitric acid, a sulfuric acid, a phosphoric acid, a fluorosulfuric acid, a chlorosulfuric acid, a tetrafluoroboric acid and a hexafluorophosphoric acid, an alkylsulfonic acid, an alkylsulfonic acid which may be halogenated, an arylsulfonic acid, an arylsulfonic acid which may have an alkyl side chain, a phosphoric acid, a carboxylic acid, and a carboxylic acid which may be halogenated.

Specific examples thereof include boron trifluoride; boron trichloride; a boron trifluoride diethyl ether complex; a boron trifluoride dimethyl sulfide complex; a salt or a complex of aluminum such as aluminum fluoride, aluminum chloride, aluminum bromide, aluminum perchlorate, aluminum nitrate, aluminum sulfate, aluminum methane sulfonate, aluminum trifluoromethane sulfonate, aluminum p-toluene sulfonate, aluminum acetate and aluminum trifluoroacetate; a salt or a complex of scandium (III) such as scandium (III) fluoride, scandium (III) chloride, scandium (III) bromide, scandium (III) perchlorate, scandium (III) nitrate, scandium (III) sulfate, scandium (III)methane sulfonate, scandium (III) trifluoromethane sulfonate, scandium (III) p-toluene sulfonate, scandium (III) acetate and scandium (III) trifluoroacetate; a salt or a complex of iron (III) such as iron (III) fluoride, iron (III) chloride, iron (III) bromide, iron (III) perchlorate, iron (III) nitrate, iron (III) sulfate, iron (III) methane sulfonate, iron (III) trifluoromethane sulfonate, iron (III) p-toluene sulfonate, iron (III) acetate and iron (III) trifluoroacetate; a salt or a complex of zinc (II) such as zinc fluoride, zinc chloride, zinc bromide, zinc perchlorate, zinc nitrate, zinc sulfate, zinc methane sulfonate, zinc trifluoromethane sulfonate, zinc p-toluene sulfonate, zinc acetate and zinc trifluoroacetate; and a salt or a complex of zirconium (IV) such as zirconium (IV) fluoride, zirconium (IV) chloride, zirconium (IV) bromide, zirconium (IV) perchlorate, zirconium (IV) nitrate, zirconium (IV) sulfate, zirconium (IV) methane sulfonate, zirconium (IV) trifluoromethane sulfonate, zirconium (IV) p-toluene sulfonate, zirconium (IV) acetate and zirconium (IV) trifluoroacetate.

Examples thereof further include a salt or a complex of indium (III) such as indium (III) fluoride, indium (III) chloride, indium (III) bromide, indium (III) perchlorate, indium (III) nitrate, indium (III) sulfate, indium (III) methane sulfonate, indium (III) trifluoromethane sulfonate, indium (III) p-toluene sulfonate, indium (III) acetate and indium (III) trifluoroacetate; a salt or a complex of bismuth (III) such as bismuth (III) fluoride, bismuth (III) chloride, bismuth (III) bromide, bismuth (III) perchlorate, bismuth (III) nitrate, bismuth (III) sulfate, bismuth (III) methane sulfonate, bismuth (III) trifluoromethane sulfonate, bismuth (III) p-toluene sulfonate, bismuth (III) acetate and bismuth (III) trifluoroacetate; and tin (IV) chloride, antimony (V) chloride, tellurium (IV) chloride, tellurium (IV) bromide, molybdenum (VI) chloride, titanium (IV) tetrachloride and vanadium (IV) tetrachloride.

Among them, boron trifluoride, boron trichloride, a boron trifluoride diethyl ether complex, a boron trifluoride dimethyl sulfide complex, aluminum fluoride, aluminum chloride, aluminum bromide, aluminum perchlorate, aluminum nitrate, aluminum sulfate, aluminum methane sulfonate, aluminum trifluoromethane sulfonate, aluminum p-toluene sulfonate, aluminum acetate, aluminum trifluoroacetate, iron (III) fluoride, iron (III) chloride, iron (III) bromide, iron (III) perchlorate, iron (III) nitrate, iron (III) sulfate, iron (III) methane sulfonate, iron (III) trifluoromethane sulfonate, iron (III) p-toluene sulfonate, iron (III) acetate, iron (III) trifluoroacetate, zinc fluoride, zinc chloride, zinc bromide, zinc perchlorate, zinc nitrate, zinc sulfate, zinc methane sulfonate, zinc trifluoromethane sulfonate, zinc p-toluene sulfonate, zinc acetate, zinc trifluoroacetate, indium (III) fluoride, indium (III) chloride, indium (III) bromide, indium (III) perchlorate, indium (III) nitrate, indium (III) sulfate, indium (III) methane sulfonate, indium (III) trifluoromethane sulfonate, indium (III) p-toluene sulfonate, indium (III) acetate, indium (III) trifluoroacetate, bismuth (III) fluoride, bismuth (III) chloride, bismuth (III) bromide, bismuth (III) perchlorate, bismuth (III) nitrate, bismuth (III) sulfate, bismuth (III) methane sulfonate, bismuth (III) trifluoromethane sulfonate, bismuth (III) p-toluene sulfonate, bismuth (III) acetate, bismuth (III) trifluoroacetate, tin (IV) chloride and molybdenum (VI) chloride are preferable.

In order to further improve the reactivity, aluminum trifluoromethane sulfonate, aluminum trifluoroacetate, iron (III) trifluoromethane sulfonate, iron (III) trifluoroacetate, zinc methane sulfonate, zinc trifluoromethane sulfonate, indium (III) methane sulfonate, indium (III) trifluoromethane sulfonate, bismuth (III) methane sulfonate and bismuth (III) trifluoromethane sulfonate are further preferable.

In order to further improve the reactivity, aluminum trifluoromethane sulfonate, iron (III) trifluoromethane sulfonate, indium (III) trifluoromethane sulfonate and bismuth (III) trifluoromethane sulfonate are particularly preferable.

Specific examples of the solid acid include an oxide such as silica and α-alumina; an amorphous or crystalline composite metal oxide such as silica alumina, silica titania, zeolite, alumina titania, titania zinc oxide, silica zinc oxide, titania zirconia and silica molybdenum; and an immobilized acid obtained by adsorbing and immobilizing liquid acid such as liquid phosphoric acid catalyst to an inorganic carrier.

Among the solid acids, silica alumina, silica titania and zeolite are preferable. The size and shape of these solid acid catalysts are not particularly limited, and a powder shape is typically useful, and the particle size thereof is preferably in a range of 10 µm to 10 mm. Particularly, in order to increase the reaction efficiency, it is preferable that they are porous and a substantial surface area (reaction solution contact area) of them is large.

These acid catalyst can be used alone, or two or more kinds thereof can be used in combination, and the use amount thereof is in a range of 0.001 to 10 equivalents, is preferably in a range of 0.005 to 5 equivalents, and is further preferably in a range of 0.01 to 2.5 equivalents, with respect to the naphthol derivative (A).

A reaction temperature is not particularly limited as long as the sulfide derivative (C) can be obtained, and the reaction temperature is in a range of 0° C. to 250° C., is preferably in a range of 25° C. to 200° C., and is further preferably in a range of 40° C. to 150° C.

A reaction time is not particularly limited as long as the sulfide derivative (C) can be obtained, and the reaction time is in a range of 10 minutes to 72 hours, is preferably in a range of 30 minutes to 48 hours, and is further preferably in a range of 1 to 24 hours.

A solvent is not particularly limited as long as it is inert to the reaction, and examples thereof include an ether solvent such as diethyl ether, tetrahydrofuran, 1,4-dioxane, dimethoxyethane and dibutyl ether; an ester solvent such as ethyl acetate, isopropyl acetate and amyl acetate; an aliphatic hydrocarbon solvent such as n-hexane, heptane, octane, cyclohexane and cyclopentane; a halogenated solvent such as dichloromethane, chloroform, carbon tetrachloride and 1,2-dichloroethane; an aromatic hydrocarbon solvent such as toluene, benzene and xylene; an amide solvent such as N,N-dimethyl formamide, N,N-dimethyl acetamide and N-methyl pyrrolidinone; a sulfur-containing solvent such as dimethyl sulfoxide and sulfolane; a nitrile solvent such as acetonitrile, valeronitrile and benzonitrile; and a carboxylic acid solvent such as an acetic acid, a propionic acid and a butyric acid, and theses solvents can be used alone, or two or more kinds thereof can be used in combination.

In the first step of the present invention, water generated as the reaction proceeds is not required to remove, but it may be continuously removed from the system by using a Dean-Stark apparatus, a distillation column or the like, and it may be removed by adding a dehydrating agent such as sodium sulfate, magnesium sulfate and zeolite.

Regarding the reaction atmosphere, the reaction can be performed in the air, but it is preferably performed in a nitrogen or argon atmosphere.

The sulfide derivative (C) obtained in the first step may be appropriately purified. The purification method is not particularly limited, and examples thereof include column chromatography, recrystallization and sublimation purification.

Next, a second step will be described.

In the second step, by dehydration reaction in the presence of a transition metal salt or a transition metal complex, the sulfide derivative (C) is converted into the dinaphthothiophene derivative (D) which is a target compound. The transition metal used for the reaction includes metal from Sc to Zn which are first transition elements, Y to Cd which are second transition elements, and La to Hg which are third transition elements. Among the transition metal, iron, cobalt, nickel, copper, molybdenum, ruthenium, rhodium, palladium, osmium, iridium, platinum and gold are preferable, and in order to further improve the reactivity, nickel, molybdenum, ruthenium, rhodium, palladium, iridium, platinum and gold are further preferable, and in order to further improve the reactivity, ruthenium, palladium and platinum are particularly preferable.

Examples of the transition metal salt or the transition metal complex include a salt or a complex composed of the aforementioned transition metal and an acid compound, and a salt or a complex composed of the aforementioned transition metal and a ligand: examples of an acid compound include water, hydrogen fluoride, hydrogen chloride, a hydrobromic acid, hydrogen iodide, a perchloric acid, a nitric acid, a sulfuric acid, a phosphoric acid, a fluorosulfuric acid, a chlorosulfuric acid, a tetrafluoroboric acid, a hexafluorophosphoric acid, a heteropoly acid such as a phosphotungstic acid, an alkylsulfonic acid, an alkylsulfonic acid which may be halogenated, an arylsulfonic acid, an arylsulfonic acid which may have an alkyl side chain, a phosphoric acid, a carboxylic acid and a carboxylic acid which may be halogenated; and examples of a ligand include alkene, alkyne, amine, phosphine, arsine, N-heterocyclic carbene, dibenzylideneacetone, acetylacetone, carbon monoxide, nitrile and salen.

Still further preferable examples of the above-described transition metal salt or transition metal complex specifically include a salt or a complex of palladium such as tetrakis (triphenylphosphine) palladium (0), tris(dibenzylideneacetone) dipalladium (0), bis(dibenzylideneacetone) palladium (0), bis[1,2-bis(diphenylphosphino)ethane] palladium (0), bis(tri-t-butylphosphine) palladium (0), bis(tricyclohexylphosphine) palladium (0), bis[di-tert-butyl(4-dimethylaminophenyl) phosphine] palladium (0), palladium (II) hydroxide, palladium (II) nitrate, dichlorobenzyl bis (triphenylphosphine) palladium (II), dichlorobis (triphenylphosphine) palladium (II), chloroallylpalladium (II) dimer, dichlorobis(acetonitrile) palladium (II), dichlorobis(benzonitrile) palladium (II), bis(triphenylphosphine) palladium (II) acetate, bis(triphenylphosphine) palladium (II) trifluoroacetate, dichloro(cis, cis-1,5-cyclooctanediene) palladium (II), palladium (II) acetate, palladium (II) trifluoroacetate, palladium (II) pivalate, bis(trifluoromethane sulfonic acid) tetrakis (acetonitrile) palladium (II), acetylacetone palladium (II), palladium (II) chloride, palladium (II) bromide, sodium (II) tetrachloropalladate, dichloro 2,5-norbornadiene palladium (II), (ethylenediamine) palladium (II) nitrate, dichloro[9,9-dimethyl-4,5-bis(diphenylphosphino) xanthene] palladium (II), dichloro(1,5-cyclooctadiene) palladium (II), a di-µ-chlorobis[5-hydroxy-2-[1-(hydroxyimino) ethyl] phenyl] palladium (II) dimer, a dichloro[di-tert-butyl(chloro) phosphine] palladium (II) dimer, chloro [(tri-tert-butylphosphine)-2-(2-aminobiphenyl) palladium (II), dichlorobis(tri-o-tolylphosphine) palladium (II), dichlorobis(methyldiphenylphosphine) palladium (II), palladium/carbon, palladium/alumina, palladium/barium carbonate and palladium/barium sulfate;

a salt or a complex of ruthenium such as cis-bis(2,2'-bipyridyl) dichlororuthenium (II) dihydrate, [(R)-2,2'-bis (diphenylphosphino)-1,1'-binaphthyl]ruthenium dichloride, carbonyl(dihydrido) tris(triphenylphosphine) ruthenium (II), chloronitrosyl[N,N'-bis(3,5-di-tert-butylsalicylidene)-1,1,2,2-tetramethylethylene diaminato]ruthenium (IV), a chloro(pentamethyl cyclopentadienyl) ruthenium (II) tetramer, a dichloro(p-cymene) ruthenium (II) dimer, 1-hydroxytetraphenyl cyclopentadienyl(tetraphenyl-2,4-cyclopentadien-1-one)-µ-h ydrotetracarbonyl diruthenium (II), ruthenium (III) chloride, chloro(p-cymene) ruthenium (II), chloronitrosyl ruthenium (II) monohydrate, triruthenium (0) dodecacarbonyl, tris(2,4-pentanedionato) ruthenium (III), dichlorotris(triphenylphosphine) ruthenium (II) and ruthenium/carbon;

and a salt or a complex of platinum such as tetrakis (triphenylphosphine) platinum (0), bis(tri-tert-butylphosphine) platinum (0), platinum (II) chloride, acetylacetone platinum (II), cis-diamine(1,1-cyclobutanedicarboxylato) platinum (II), dichloro cis-diammine platinum (II), dichloro(1,5-cyclooctadiene) platinum (II) and (trans-1,2-cyclohexanediamine) oxalatoplatinum (II).

The transition metal salt or transition metal complex can be used alone, or two or more kinds thereof can be used in combination, and the use amount thereof is not particularly limited as long as it is within a range where dinaphthothiophene (D) can be obtained. For example, the use amount is in a range of 0.001 to 10 equivalents, is preferably in a range of 0.005 to 5 equivalents, and is further preferably in a range of 0.01 to 2.5 equivalents, with respect to sulfide (C).

Further, in order to promote the dehydrogenation reaction, a ligand may be used in combination.

Examples of the ligand include a monodentate phosphine ligand such as trimethyl phosphine, triethyl phosphine, tri-n-butyl phosphine, tri-tert-butyl phosphine, tricyclohexylphosphine, triphenyl phosphine and tri(o-tolyl) phosphine; and a bidentate phosphine ligand such as bis(diphenylphosphino)methane, 1,2-bis(diphenylphosphino)ethane, 2,2'-bis (diphenylphosphino)-1,1'-binaphthalene and 1,1'-bis(diphenylphosphino) ferrocene.

The above-described ligands can be used alone, or two or more kinds thereof can be used in combination, and the use amount thereof is not particularly limited as long as it is within a range where dinaphthothiophene (D) can be obtained. For example, the use amount is in a range of 1 to 20 equivalents, is preferably in a range of 1 to 10 equivalents, and is further preferably in a range of 1 to 5 equivalents, with respect to the transition metal salt or transition metal complex.

In order to promote the dehydrogenation reaction, an oxidizing agent may be used in combination.

Examples of the oxidizing agent include peroxide such as a peracetic acid, hydrogen peroxide, hydrogen peroxide water, urea hydrogen peroxide, oxone, sodium percarbonate, sodium perborate, potassium perborate, dipotassium peroxodisulfate, tetrabutyl ammonium persulfate, a 3-chloroperoxy benzoic acid, dimethyl dioxirane, tert-butyl hydroperoxide and benzoyl peroxide.

Examples thereof further include high oxidation halide such as sodium hypochlorite, sodium chlorite, potassium bromate, sodium periodate and tert-butyl hypochlorite; oxidizing gas such as oxygen, ozone, fluorine, chlorine, bromine, nitric oxide and dinitrogen monoxide; a metal compound having a high degree of oxidation such as chromium trioxide, manganese dioxide, manganese (III) acetate, potassium permanganate, potassium dichromate, divanadium (V) pentoxide, triisopropoxy vanadium (V) oxide, ammonium cerium (IV) nitrate, lead (IV) acetate and osmium (VIII) oxide; and a silver (I) compound such as silver fluoride, silver chloride, silver bromide, silver iodide, silver oxide, silver carbonate, silver cyanide, silver sulfate, silver nitrate, silver acetate, silver trifluoroacetate, silver pivalate, silver lactate, silver cyclohexane butyrate, silver methane sulfonate, silver trifluoromethane sulfonate and silver tetrafluoroborate.

In addition, a copper (II) compound such as copper (II) fluoride, copper (II) chloride, copper (II) bromide, copper (II) iodide, copper (II) oxide, copper (II) carbonate, copper (II) cyanide, copper (II) sulfate, copper (II) nitrate, copper (II) acetate, copper (II) trifluoroacetate, copper (II) pivalate, copper (II) lactate, copper (II) cyclohexane butyrate, copper (II) methane sulfonate, copper (II) trifluoromethane sulfonate and copper (II) tetrafluoroborate; and an iron (II) compound such as iron (II) fluoride, iron (II) chloride, iron (II) bromide, iron (II) iodide, iron (II) oxide, iron (II) carbonate, iron (II) cyanide, iron (II) sulfate, iron (II) nitrate, iron (II) acetate, iron (II) trifluoroacetate, iron (II) pivalate, iron (II) lactate, iron (II) cyclohexane butyrate, iron (II) methane sulfonate, iron (II) trifluoromethane sulfonate and iron (II) tetrafluoroborate are also exemplified.

In addition, an iron (III) compound such as iron (III) fluoride, iron (III) chloride, iron (III) bromide, iron (III) iodide, iron (III) oxide, iron (III) carbonate, iron (III) cyanide, iron (III) sulfate, iron (III) nitrate, iron (III) acetate, iron (III) trifluoroacetate, iron (III) pivalate, iron (III) lactate, iron (III) cyclohexane butyrate, iron (III) methane sulfonate, iron (III) trifluoromethane sulfonate and iron (III) tetrafluoroborate; and a quinone derivative such as benzoquinone, anthraquinone, 2-(cyclohexyl sulfinyl)-benzoquinone, 2-(phenyl sulfinyl)-benzoquinone, 2,3-dichloro-5,6-dicyano-1,4-benzoquinone, chloranil and o-chloranil are further exemplified.

Among them, a peracetic acid, hydrogen peroxide, aqueous hydrogen peroxide, urea hydrogen peroxide, dipotassium peroxodisulfate, oxone, tetrabutyl ammonium persulfate, chromium trioxide, manganese dioxide, manganese (III) acetate, ammonium cerium (IV) nitrate, 3-chloroperbenzoic acid, oxygen, silver fluoride, silver chloride, silver bromide, silver iodide, silver oxide, silver carbonate, silver cyanide, silver sulfate, silver nitrate, silver acetate, silver trifluoroacetate, silver pivalate, silver lactate, silver cyclohexane butyrate, silver methane sulfonate, silver trifluoromethane sulfonate, silver tetrafluoroborate, copper (II) fluoride, copper (II) chloride, copper (II) bromide, copper (II) iodide, copper (II) oxide, copper (II) carbonate, copper (II) cyanide, copper (II) sulfate, copper (II) nitrate, copper (II) acetate, copper (II) trifluoroacetate, copper (II) pivalate, copper (II) lactate, copper (II) cyclohexane butyrate, copper (II) methane sulfonate, copper (II) trifluoromethane sulfonate, copper (II) tetrafluoroborate, iron (II) fluoride, iron (II) chloride, iron (II) bromide, iron (II) iodide, iron (II) oxide, iron (II) carbonate, iron (II) cyanide, iron (II) sulfate, iron (II) nitrate, iron (II) acetate, iron (II) trifluoroacetate, iron (II) pivalate, iron (II) lactate, iron (II) cyclohexane butyrate, iron (II) methane sulfonate, iron (II) trifluoromethane sulfonate and iron (II) tetrafluoroborate are preferable.

Oxygen, silver fluoride, silver chloride, silver bromide, silver iodide, silver oxide, silver carbonate, silver cyanide, silver sulfate, silver nitrate, silver acetate, silver trifluoroacetate, silver pivalate, silver lactate, silver cyclohexane butyrate, silver methane sulfonate, silver trifluoromethane sulfonate and silver tetrafluoroborate are further preferable.

Oxygen, silver nitrate, silver acetate, silver trifluoroacetate, silver pivalate, silver lactate, silver cyclohexane butyrate, silver methane sulfonate, silver trifluoromethane sulfonate and silver tetrafluoroborate are still further preferable.

Oxygen, silver acetate, silver trifluoroacetate, silver pivalate, silver lactate, silver methane sulfonate and silver trifluoromethane sulfonate are particularly preferable.

The oxidizing agent can be used alone, or two or more kinds thereof can be used in combination. The use amount thereof is not particularly limited as long as it is within a range where dinaphthothiophene (D) can be obtained. For example, the use amount is in a range of 1 to 100 equivalents, is preferably in a range of 1 to 20 equivalents, and is further preferably in a range of 1 to 10 equivalents, with respect to sulfide (C).

In order to promote the dehydrogenation reaction, a carboxylic acid may be used additionally. Examples of the carboxylic acid include a saturated aliphatic carboxylic acid such as a formic acid, an acetic acid, a propionic acid, a butyric acid, a valeric acid, a caproic acid, an enanthic acid, a caprylic acid, a pelargonic acid, a capric acid, a lauric acid, a myristic acid, a palmitic acid, a margaric acid, a stearic acid, a pivalic acid, a 2,2-dimethylbutyric acid, a 1-methyl-1-cyclohexane carboxylic acid and a 2-phenyl isobutyric acid; and an unsaturated aliphatic carboxylic acid such as an oleic acid, a linoleic acid, a linolenic acid, an arachidonic acid and an eicosapentaenoic acid.

Examples thereof further include a saturated aliphatic carboxylic acid, which is halogenated, such as a fluoroacetic acid, a trifluoroacetic acid, a chloroacetic acid, a dichloroacetic acid and a trichloroacetic acid; an aromatic carboxylic acid such as a benzoic acid, a phthalic acid, an isophthalic acid, a terephthalic acid, a salicylic acid, a gallic acid, a mellitic acid, and a cinnamic acid; and a multivalent carboxylic acid such as an oxalic acid, a maleic acid, a fumaric acid, a succinic acid, a glutaric acid, a muconic acid, an adipic acid, an azelaic acid, a 2,5-thiophene dicarboxylic acid, a terephthalic acid, a 2,5-pyrazine dicarboxylic acid, a naphthalene-2,6-dicarboxylic acid, a biphenyl-4,4'-dicarboxylic acid, an azobenzene dicarboxylic acid, a benzene-1,2,4-tricarboxylic acid, a benzene-1,3,5-tribenzoic acid, a benzene-1,2,4,5-tetracarboxylic acid, a naphthalene-2,3,6,7-tetracarboxylic acid, a naphthalene-1,4,5,8-tetracarboxylic acid, a biphenyl-3,5,3',5'-tetracarboxylic acid, a 2-amino terephthalic acid, a 2-nitroterephthalic acid, a 2-methyl terephthalic acid, a 2-chloroterephthalic acid, a 2-bromoterephthalic acid, a 2,5-dihydroxyterephthalic acid, a tetrafluoroterephthalic acid, a 2,5-dicarboxylic terephthalic acid, a dimethyl-4,4'-biphenyl dicarboxylic acid, a tetramethyl-4,4'-biphenyl dicarboxylic acid, a dicarboxy-4,4'-biphenyl dicarboxylic acid, a 2,5-pyrazine dicarboxylic acid, a 2,5-diperfluoroterephthalic acid, an azobenzene-4,4'-dicarboxylic acid, a 3,3'-dichloroazobenzene-4,4'-dicarboxylic acid, a 3,3'-dihydroxyazobenzene-4,4'-dicarboxylic acid, a 3,3'-diperfluoroazobenzene-4,4'-dicarboxylic acid, a 3,5,3',5'-azobenzene tetracarboxylic acid and a 2,5-dimethyl terephthalic acid.

A formic acid, an acetic acid, a propionic acid, a butyric acid, a valeric acid, a caproic acid, an enanthic acid, a caprylic acid, a pelargonic acid, a capric acid, a lauric acid, a myristic acid, a palmitic acid, a margaric acid, a stearic acid, a pivalic acid, a 2,2-dimethyl butyric acid, a 1-methyl-1-cyclohexane carboxylic acid, a 2-phenyl isobutyric acid, an oleic acid, a linoleic acid, a linolenic acid, an arachidonic acid, an eicosapentaenoic acid, a fluoroacetic acid, a trifluoroacetic acid, a chloroacetic acid, a dichloroacetic acid, a trichloroacetic acid, a benzoic acid, a phthalic acid, an isophthalic acid, a terephthalic acid, a salicylic acid, a gallic acid, a mellitic acid and a cinnamic acid are preferable.

A formic acid, an acetic acid, a propionic acid, a butyric acid, a valeric acid, a caproic acid, an enanthic acid, a caprylic acid, a pelargonic acid, a capric acid, a lauric acid, a myristic acid, a palmitic acid, a margaric acid, a stearic acid, a pivalic acid, a 2,2-dimethylbutyric acid, a 1-methyl-1-cyclohexane carboxylic acid, a 2-phenyl isobutyric acid, a fluoroacetic acid, a trifluoroacetic acid, a chloroacetic acid, a dichloroacetic acid, and a trichloroacetic acid are further preferable, and an acetic acid, a propionic acid, a pivalic acid, a 2,2-dimethylbutyric acid, a 1-methyl-1-cyclohexanecarboxylic acid, a trifluoroacetic acid and a trichloroacetic acid are still further preferable.

The carboxylic acid can be used alone, or two or more kinds thereof can be used in combination, and the use amount thereof is not particularly limited as long as it is within a range where dinaphthothiophene (D) can be obtained. For example, the use amount is in a range of 1 to 1000 equivalents, is preferably in a range of 1 to 500 equivalents, and is further preferably in a range of 1 to 100 equivalents, with respect to the transition metal salt or complex.

In order to promote the dehydrogenation reaction, a base may be used in combination.

Examples of the base include carbonate such as sodium carbonate, potassium carbonate and cesium carbonate; phosphate such as sodium phosphate, disodium phosphate, trisodium phosphate, potassium phosphate, calcium phosphate, and diammonium phosphate; hydroxide such as lithium hydroxide, sodium hydroxide, potassium hydroxide and cesium hydroxide; fluoride such as potassium fluoride, cesium fluoride, and tetrabutyl ammonium fluoride; alkoxides such as sodium methoxide, sodium ethoxide and potassium tert-butoxide; tertiary amine such as trimethyl amine, triethyl amine, tributyl amine, diisopropyl ethyl amine, N-methyl morpholine, N-methyl pyrrolidine, N-methyl piperidine, 1,8-diaza-bicyclo[5.4.0]undeca-7-ene and 1,4-diaza-bicyclo[2.2.2]octane; and a pyridine derivative such as pyridine, picoline, ethyl pyridine, propyl pyridine, butyl pyridine, t-butyl pyridine, 2,3-dimethyl pyridine, 2,4-dimethyl pyridine, 2,5-dimethyl pyridine, 2,6-dimethyl pyridine, 3,5-dimethyl pyridine, 2-methyl-5-ethyl-pyridine, 2,6-diisopropyl pyridine and 2,6-di-t-butyl pyridine.

Sodium carbonate, potassium carbonate, cesium carbonate, sodium phosphate, disodium phosphate, trisodium phosphate, potassium phosphate, calcium phosphate, diammonium phosphate, lithium hydroxide, sodium hydroxide, potassium hydroxide, cesium hydroxide, potassium fluoride, cesium fluoride, tetrabutyl ammonium fluoride, sodium methoxide, sodium ethoxide, potassium tert-butoxide, trimethyl amine, triethyl amine, tributyl amine, diisopropyl ethyl amine, N-methyl morpholine, N-methyl pyrrolidine, N-methyl piperidine, 1,8-diaza-bicyclo[5.4.0]undec-7-ene and 1,4-diaza-bicyclo[2.2.2]octane are preferable.

Sodium carbonate, potassium carbonate, cesium carbonate, sodium phosphate, disodium phosphate, trisodium phosphate, potassium phosphate, calcium phosphate, diammonium phosphate, lithium hydroxide, sodium hydroxide, potassium hydroxide, cesium hydroxide, fluoride such as potassium fluoride, cesium fluoride and tetrabutyl ammonium fluoride, sodium methoxide, sodium ethoxide, and potassium tert-butoxide are further preferable.

Sodium carbonate, potassium carbonate, cesium carbonate, sodium phosphate, disodium phosphate, trisodium phosphate, potassium phosphate, calcium phosphate, diammonium phosphate, lithium hydroxide, sodium hydroxide, potassium hydroxide and cesium hydroxide are particularly preferable.

The base can be used alone, or two or more kinds thereof can be used in combination. The use amount thereof is not particularly limited as long as it is within a range where dinaphthothiophene (D) can be obtained. For example, the use amount is in a range of 1 to 100 equivalents, is preferably in a range of 1 to 20 equivalents, and is further preferably in a range of 1 to 10 equivalents, with respect to sulfide (C).

A reaction temperature is not particularly limited as long as the dinaphthothiophene derivative (D) can be obtained, and the reaction temperature is in a range of 0° C. to 250° C., is preferably in a range of 10° C. to 200° C., and is further preferably in a range of 25° C. to 160° C.

A reaction time is not particularly limited as long as the dinaphthothiophene derivative (D) can be obtained, and the reaction time is in a range of 10 minutes to 72 hours, is preferably in a range of 30 minutes to 48 hours, and is further preferably in a range of 1 to 24 hours.

A solvent may be used, but a solvent may not be indispensable. In a case where a solvent is used, it is not particularly limited as long as it is inert to the reaction, and examples thereof include an ether solvent such as diethyl ether, tetrahydrofuran, 1,4-dioxane, dimethoxyethane and dibutyl ether; an ester solvent such as ethyl acetate, isopropyl acetate and amyl acetate; an aliphatic hydrocarbon solvent such as n-hexane, heptane, octane, cyclohexane and cyclopentane; a halogenated solvent such as dichloromethane, chloroform, carbon tetrachloride and 1,2-dichloroethane; an aromatic hydrocarbon solvent such as toluene, benzene and xylene; an amide solvent such as N,N-dimethyl formamide, N,N-dimethyl acetamide and N-methyl pyrodinone; a sulfur-containing solvent such as dimethyl sulfoxide and sulfolane; a nitrile solvent such as acetonitrile, valeronitrile and benzonitrile; and a carboxylic acid solvent such as an acetic acid, a propionic acid and a butyric acid. Theses solvents can be used alone, or two or more kinds thereof can be used in combination.

The reaction atmosphere is not particularly limited. For example, air, oxygen, nitrogen, argon and carbon dioxide can be employed. When oxygen is used as an oxidizing agent, it can be performed under air or oxygen.

The dinaphthothiophene derivative (D) obtained by the second step may be appropriately purified. The purification method is not particularly limited, and examples thereof include column chromatography, recrystallization and sublimation purification.

Dinaphthothiophene Derivative

Hereinafter, the dinaphthothiophene derivative of the present invention will be described.

The dinaphthothiophene derivative of the present invention is a compound represented by General Formula (E). Here, a compound (E-a), a compound (E-b), a compound (E-c), a compound (E-d), a compound (E-e), a compound (E-f), a compound (E-g), a compound (E-h), a compound (E-i), a compound (E-j), a compound (E-k) and a compound (E-L) are excluded.

[Chem. 6]

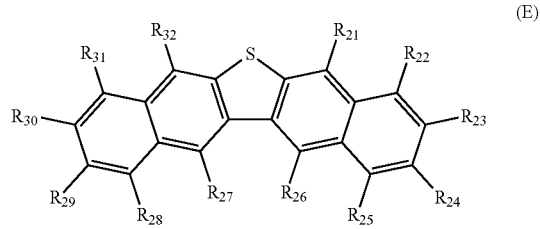

(E)

In the formula, $R_{21}$ to $R_{32}$ are a hydrogen atom or an arbitrary substituent, wherein $R_{21}$ and $R_{32}$ are the same as or different from each other, $R_{22}$ and $R_{31}$ are the same as or different from each other, $R_{23}$ and $R_{30}$ are the same as or different from each other, $R_{24}$ and $R_{29}$ are the same as or different from each other, $R_{25}$ and $R_{28}$ are the same as or different from each other, and $R_{26}$ and $R_{27}$ are the same as or different from each other provided that, in terms of at least one combination of the six combinations of $R_{21}$ and $R_{32}$, $R_{22}$ and $R_{31}$, $R_{23}$ and $R_{30}$, $R_{24}$ and $R_{29}$, $R_{25}$ and $R_{28}$, and $R_{26}$ and $R_{27}$, the two substituents which constitute the combination are different from each other.

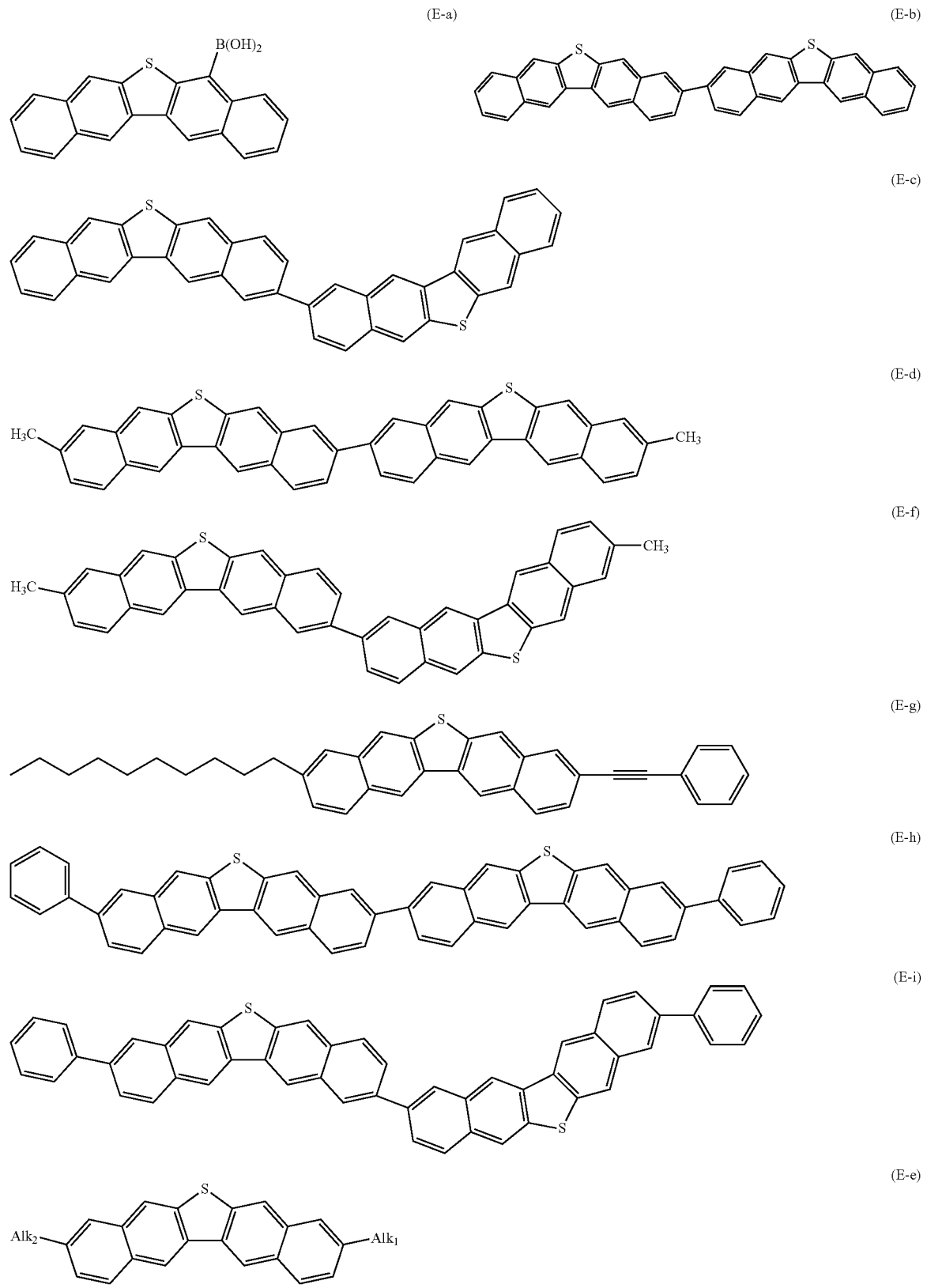

In the formula, Alk1 and Alk2 represent a linear alkyl group having 1 to 30 carbon atoms.

[Chem. 8]

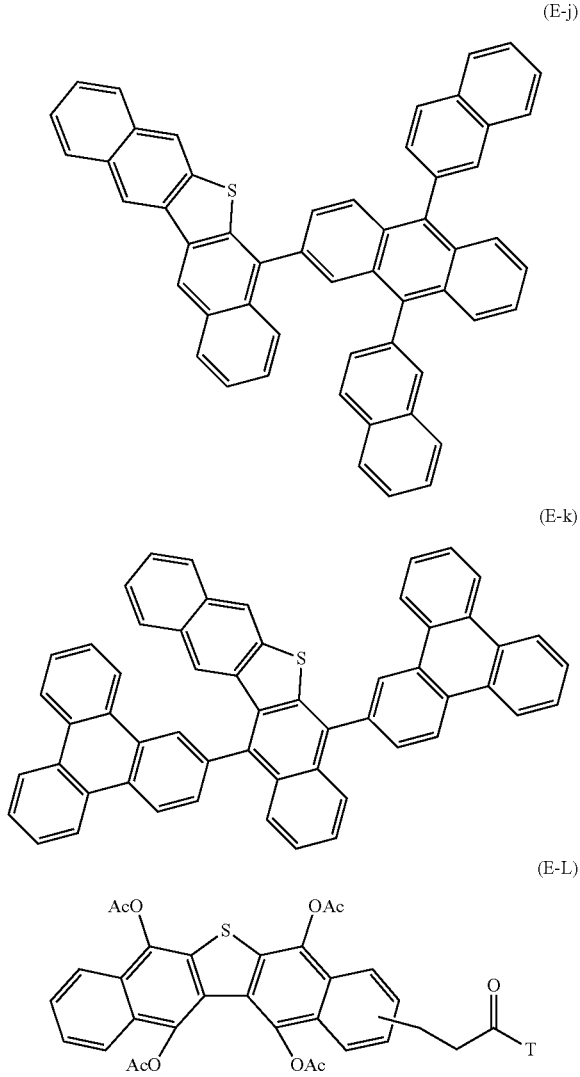

(E-j)

(E-k)

(E-L)

The feature of the compound of the present invention is that, in terms of at least one combination of the six combinations relating to the substituent, the two substituents which constitute the at least one combination are different from each other. In a case where the six combinations are the combinations having the same substituents, that is, $R_{21}$ and $R_{32}$ are the same as each other, $R_{22}$ and $R_{31}$ are the same as each other, $R_{23}$ and $R_{30}$ are the same as each other, $R_{24}$ and $R_{29}$ are the same as each other, $R_{25}$ and $R_{28}$ are the same as each other, and $R_{26}$ and $R_{27}$ are the same as each other, the molecular symmetry becomes $C_{2v}$ and, since its symmetry is high, then its crystallinity is increased. For this reason, the intermolecular force is excessively increased, the film quality of polycrystalline film, prepared by dropping or drop-casting a solution or ink and drying it, is lowered, and thereby the semiconductor properties are deteriorated. Generally, such an intermolecular force generates large crystal grains, lowering the homogeneity of the film. On the other hand, in the compound of the present invention, the symmetry is low, the intermolecular force is moderately optimized, the film quality of polycrystalline film, prepared by dropping or drop-casting a solution or ink and then drying it, is high, and thereby the semiconductor properties are improved.

From such a viewpoint, as a position structure of the substituent, it is preferable that in terms of at least one combination of the six combinations of $R_{21}$ and $R_{32}$, $R_{22}$ and $R_{31}$, $R_{23}$ and $R_{30}$, $R_{24}$ and $R_{29}$, $R_{25}$ and $R_{29}$, and $R_{26}$ and $R_{27}$, the two substituents which constitute the at least one combination are different from each other, and the two substituents which constitute each of the other combinations are the same as each other and are hydrogen atoms.

In order to obtain a compound having higher mobility, it is particularly preferable that among the six combinations of $R_{21}$ and $R_{32}$, $R_{22}$ and $R_{31}$, $R_{23}$ and $R_{30}$, $R_{24}$ and $R_{29}$, $R_{25}$ and $R_{28}$, and $R_{26}$ and $R_{27}$; $R_{21}$ and $R_{32}$, $R_{22}$ and $R_{31}$, $R_{25}$ and $R_{28}$, and $R_{26}$ and $R_{27}$ are the same as each other and are hydrogen atoms, $R_{23}$ and $R_{30}$ are the same as or different from each other, $R_{24}$ and $R_{29}$ are the same as or different from each other, and in terms of at least one combination of two combinations of $R_{23}$ and $R_{30}$, and $R_{24}$ and $R_{29}$, the two substituents which constitute the at least one combination are different from each other.

Next, substituents of the compound of the present invention will be described.

The substituents $R_{21}$ to $R_{32}$ of the compound represented by General Formula (E) of the present invention are not limited as long as they are conventionally well-known as substituents of an aromatic compound. For example, examples thereof include a group selected from an acyclic or cyclic alkyl group having 1 to 20 carbon atoms wherein at least one hydrogen atom in the alkyl group may be substituted with an aromatic group, a halogeno group or a nitrile group, and at least one —CH$_2$— in the alkyl group may be replaced by —O—, —R'C=CR'—, —CO—, —OCO—, —COO—, —S—, —SO$_2$—, —SO—, —NH—, —NR'— or —C≡— provided that, with respect to each of an oxygen atom, a sulfur atom and a nitrogen atom, the same atoms are not directly bonded to each other, wherein R' represents an acyclic or cyclic alkyl group having 1 to 20 carbon atoms; a halogeno group; an aromatic group wherein the aromatic group may be substituted with an acyclic or cyclic alkyl group having 1 to 20 carbon atoms, a halogeno group, an aromatic group or a nitrile group, wherein at least one hydrogen atom in the alkyl group may be substituted with an aromatic group, a halogeno group or a nitrile group, and at least one —CH$_2$— in the alkyl group may be replaced by —O—, —CR"=CR"—, —CO—, —OCO—, —COO—, —S—, —SO$_2$—, —SO—, —NH—, —NR"—, or —C≡— provided that, with respect to each of an oxygen atom, a sulfur atom and a nitrogen atom, the same atoms are not directly bonded to each other, wherein R" represents an acyclic or cyclic alkyl group having 1 to 20 carbon atoms; a nitro group; and a nitrile group.

Specifically, examples of the acyclic or cyclic alkyl group having 1 to 20 carbon atoms wherein at least one hydrogen atom in the alkyl group may be substituted with an aromatic group, a halogeno group or a nitrile group, and at least one —CH$_2$— in the alkyl group may be replaced by —O—, —R'C=CR'—, —CO—, —OCO—, —COO—, —S—, —SO$_2$—, —SO—, —NH—, —NR'— or —C≡— provided that, with respect to each of an oxygen atom, a sulfur atom and a nitrogen atom, the same atoms are not directly bonded to each other, wherein R' represents an acyclic or cyclic alkyl group having 1 to 20 carbon atoms include (A-1) linear or branched alkyl group having 1 to 20 carbon atoms, (A-2)

alicyclic alkyl group having 3 to 20 carbon atoms, (A-3) alkoxy group having 1 to 19 carbon atoms, (A-4) alkoxyalkyl group having 2 to 19 carbon atoms, (A-5) alkenyl group having 2 to 20 carbon atoms, (A-6) alkanoyl group having 2 to 20 carbon atoms, (A-7) alkanoylalkyl group having 3 to 20 carbon atoms, (A-8) alkoxycarbonyl group having 2 to 20 carbon atoms, (A-9) alkanoyloxy group having 2 to 20 carbon atoms, (A-10) alkyl sulfanyl group having 1 to 19 carbon atoms, (A-11) alkyl sulfanylalkyl group having 2 to 19 carbon atoms, (A-12) alkyl sulfonyl group having 1 to 19 carbon atoms, (A-13) alkyl sulfonyl alkyl group having 2 to 19 carbon atoms, (A-14) alkyl sulfinyl group having 1 to 19 carbon atoms, (A-15) alkyl sulfinyl alkyl group having 2 to 19 carbon atoms, (A-16) alkyl amino group having 1 to 19 carbon atoms, (A-17) alkyl amino alkyl group having 2 to 19 carbon atoms, (A-18) alkynyl group having 2 to 20 carbon atoms, and (A-19) alkynyl group substituted with an aromatic hydrocarbon group which may have a substituent or an alkynyl group substituted with a heteroaromatic group which may have a substituent.

Among the above-described (A-1) to (A-19), from the viewpoint of improving the film forming property and the mobility of the compound of the present invention, as the (A-1), a linear or branched alkyl group having 1 to 20 carbon atoms; as the (A-2), an alicyclic alkyl group having 3 to 20 carbon atoms; as the (A-3), an alkoxy group having 1 to 19 carbon atoms; as the (A-4), an alkoxyalkyl group having 2 to 19 carbon atoms; as the (A-5), an alkenyl group having 2 to 20 carbon atoms; as the (A-10), an alkyl sulfanyl group having 1 to 19 carbon atoms; as the (A-11), an alkyl sulfanylalkyl group having 2 to 19 carbon atoms; as the (A-18), an alkynyl group having 2 to 20 carbon atoms; and as the (A-19), an alkynyl group substituted with an aromatic hydrocarbon group which may have a substituent or an alkynyl group substituted with a heteroaromatic group which may have a substituent; is preferable, and in order to obtain a compound having higher mobility, as the (A-1), a linear or branched alkyl group having 1 to 20 carbon atoms; as the (A-4), an alkoxyalkyl group having 2 to 19 carbon atoms; and as the (A-19), an alkynyl group substituted with an aromatic hydrocarbon group which may have a substituent or an alkynyl group substituted with a heteroaromatic group which may have a substituent; is particularly preferable.

Specific examples of the (A-1) include a linear alkyl group such as a methyl group, an ethyl group, an n-propyl group, an n-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group and an n-eicosyl group; a branched alkyl group such as an isopropyl group, an isobutyl group, an isopentyl group, a neopentyl group, a 1-methylpentyl group, a 4-methyl-2-pentyl group, a 3,3-dimethyl butyl group, a 2-ethyl butyl group, a 1-methyl hexyl group, a cyclohexyl methyl group, a tert-octyl group, a 1-methyl heptyl group, a 2-ethyl hexyl group, a 3-ethyl heptyl group, a 2-propyl pentyl group, a 2,2-dimethyl heptyl group, a 2,6-dimethyl-4-heptyl group, a 3,5,5-trimethyl hexyl group, a 1-methyl decyl group and a 1-hexyl heptyl group; and a cyclic alkyl group such as a cyclopentyl group, a cyclohexyl group, a 4-methyl cyclohexyl group, a cycloheptyl group and a cyclooctyl group.

Specific examples of the (A-4) include a 2-methoxyethyl group, a 2-ethoxyethyl group, a 2-n-propoxyethyl group, a 2-isopropoxyethyl group, a 2-n-butoxyethyl group, a 2-n-hexyloxyethyl group, a 2-(2'-ethyl butyloxy) ethyl group, a 2-n-heptyloxyethyl group, a 2-n-octyloxyethyl group, a 2-(2'-ethyl hexyloxy) ethyl group, a 2-n-decyloxyethyl group, a 2-n-dodecyloxyethyl group, a 2-n-tetradecyloxyethyl group, a 2-cyclohexyloxyethyl group, a 2-methoxypropyl group, a 3-methoxypropyl group, a 3-ethoxypropyl group, a 3-n-propoxypropyl group, a 3-isopropoxypropyl group, a 3-n-butoxypropyl group, a 3-n-pentyloxypropyl group, a 3-n-hexyloxypropyl group, a 3-(2'-ethylbutyoxy) propyl group, a 3-n-octyloxypropyl group, a 3-(2'-ethyl hexyloxy) propyl group, a 3-n-decyloxypropyl group, a 3-n-dodecyloxypropyl group, a 3-n-tetradecyloxypropyl group, a 3-cyclohexyloxypropyl group, a 4-methoxybutyl group, a 4-ethoxybutyl group, a 4-n-propoxybutyl group, a 4-isopropoxybutyl group, a 4-n-butoxybutyl group, a 4-n-hexyloxybutyl group, a 4-n-octyloxybutyl group, a 4-n-decyloxybutyl group, a 4-n-dodecyloxybutyl group, a 5-methoxypentyl group, a 5-ethoxypentyl group, a 5-n-propoxypentyl group, a 5-n-pentyloxypentyl group, a 6-methoxyhexyl group, a 6-ethoxyhexyl group, a 6-isopropoxyhexyl group, a 6-n-butoxyhexyl group, a 6-n-hexyloxyhexyl group, a 6-n-decyloxyhexyl group, a 4-methoxycyclohexyl group, a 7-methoxyheptyl group, a 7-ethoxyheptyl group, a 7-isopropoxyheptyl group, a 8-methoxyoctyl group, a 8-ethoxyoctyl group, a 9-methoxynonyl group, a 9-ethoxynonyl group, a 10-methoxydecyl group, a 10-ethoxydecyl group, a 10-n-butoxydecyl group, a 11-methoxyundecyl group, a 12-methoxydodecyl group, a 12-ethoxydodecyl group, a 12-isopropoxydodecyl group, a 14-methoxytetradecyl group, a cyclohexyloxyethyl group and a cyclohexyloxypropyl group.

Specific examples of the (A-19) include an ethynyl group substituted with a phenyl group which may have a substituent, represented by General Formula (A-19-1), and an ethynyl group substituted with a thienyl group which may have a substituent represented by General Formula (A-19-2). Specific examples of the substituent include a linear or branched alkyl group having 1 to 20 carbon atoms.

[Chem. 9]

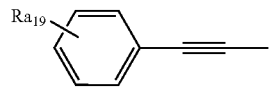

(A-19-1)

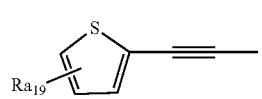

(A-19-2)

$Ra_{19}$ represents an arbitrary substituent.

Specifically, the halogeno group is a fluoro group (fluorine atom), a chloro group (chlorine atom), a bromo group (bromine atom) and an iodo group (iodine atom).

Among the above-described halogeno groups, from the viewpoint of improving film forming property and mobility of the compound of the present invention, a fluoro group and a chloro group are preferable, and a fluoro group is particularly preferable in order to obtain a compound having higher mobility.

Specifically, examples of the aromatic group wherein the aromatic group may be substituted with an acyclic or cyclic alkyl group having 1 to 20 carbon atoms, a halogeno group, an aromatic group or a nitrile group, wherein at least one hydrogen atom in the alkyl group may be substituted with an aromatic group, a halogeno group or a nitrile group, and at least one —CH$_2$— in the alkyl group may be replaced by —O—, —CR"=CR"—, —CO—, —OCO—, —OCO—, —S—, —SO$_2$—, —SO—, —NH—, —NR"— or —C≡C— wherein R" represents an acyclic or cyclic alkyl group having 1 to 20 carbon atoms provided that, with respect to each of an oxygen atom, a sulfur atom and a nitrogen atom, the same atoms are not directly bonded to each other include (B-1) an unsubstituted aromatic hydrocarbon group or an unsubstituted heteroaromatic group, (B-2) a halogenated aromatic hydrocarbon group or a halogenated heteroaromatic group, (B-3) an aromatic hydrocarbon group or a heteroaromatic group in which an aromatic hydrocarbon group or a heteroaromatic group is connected through a single bond, (B-4) a nitrileated aromatic hydrocarbon group or a nitrileated heteroaromatic group, (B-5) an aromatic hydrocarbon group or a heteroaromatic group which is substituted with a linear or branched alkyl group having 1 to 20 carbon atoms, (B-6) an aromatic hydrocarbon group or a heteroaromatic group which is substituted with an alicyclic alkyl group having 3 to 20 carbon atoms, (B-7) an aromatic hydrocarbon group or a heteroaromatic group which is substituted with an alkoxy group having 1 to 19 carbon atoms, (B-8) an aromatic hydrocarbon group or a heteroaromatic group which is substituted with an alkoxyalkyl group having 2 to 19 carbon atoms, (B-9) an aromatic hydrocarbon group or a heteroaromatic group which is substituted with an alkenyl group having 2 to 20 carbon atoms, (B-10) an aromatic hydrocarbon group or a heteroaromatic group which is substituted with an alkanoyl group having 2 to 20 carbon atoms, (B-11) an aromatic hydrocarbon group or a heteroaromatic group which is substituted with an alkanoylalkyl group having 3 to 20 carbon atoms, (B-12) an aromatic hydrocarbon group or a heteroaromatic group which is substituted with an alkoxycarbonyl group having 2 to 20 carbon atoms, (B-13) an aromatic hydrocarbon group or a heteroaromatic group which is substituted with an alkanoyloxy group having 2 to 20 carbon atoms, (B-14) an aromatic hydrocarbon group or a heteroaromatic group which is substituted with an alkyl sulfanyl group having 1 to 19 carbon atoms, (B-15) an aromatic hydrocarbon group or a heteroaromatic group which is substituted with an alkyl sulfanylalkyl group having 2 to 19 carbon atoms, (B-16) an aromatic hydrocarbon group or a heteroaromatic group which is substituted with an alkyl sulfonyl group having 1 to 19 carbon atoms, (B-17) an aromatic hydrocarbon group or a heteroaromatic group which is substituted with an alkyl sulfonyl alkyl group having 2 to 19 carbon atoms, (B-18) an aromatic hydrocarbon group or a heteroaromatic group which is substituted with an alkyl sulfinyl group having 1 to 19 carbon atoms, (B-19) an aromatic hydrocarbon group or a heteroaromatic group which is substituted with an alkyl sulfinyl alkyl group having 2 to 19 carbon atoms, (B-20) an aromatic hydrocarbon group or a heteroaromatic group which is substituted with an alkyl amino group having 1 to 19 carbon atoms, (B-21) an aromatic hydrocarbon group or a heteroaromatic group which is substituted with an alkyl amino alkyl group having 2 to 19 carbon atoms, and (B-22) an aromatic hydrocarbon group or a heteroaromatic group which is substituted with an alkynyl group having 2 to 20 carbon atoms.

Among the above-described (B-1) to (B-22), from the viewpoint of improving the film forming property and mobility of the compound of the present invention, as the (B-1), an unsubstituted aromatic hydrocarbon group or unsubstituted heteroaromatic group; as the (B-2), a halogenated aromatic hydrocarbon group or halogenated heteroaromatic group; as the (B-3), an aromatic hydrocarbon group or heteroaromatic group wherein an aromatic hydrocarbon group or a heteroaromatic group is connected through a single bond; as the (B-5), an aromatic hydrocarbon group or heteroaromatic group which is substituted with a linear or branched alkyl group having 1 to 20 carbon atoms; as the (B-6), an aromatic hydrocarbon group or heteroaromatic group which is substituted with an alicyclic alkyl group having 1 to 20 carbon atoms; as the (B-7), an aromatic hydrocarbon group or heteroaromatic group which is substituted with an alkoxy group having 1 to 19 carbon atoms; as the (B-8), an aromatic hydrocarbon group or heteroaromatic group which is substituted with an alkoxyalkyl group having 2 to 19 carbon atoms; as the (B-9), an aromatic hydrocarbon group or heteroaromatic group which is substituted with an alkenyl group having 2 to 20 carbon atoms; as the (B-14), an aromatic hydrocarbon group or heteroaromatic group which is substituted with an alkyl sulfanyl group having 1 to 19 carbon atoms; as the (B-15), an aromatic hydrocarbon group or heteroaromatic group which is substituted with an alkyl sulfanylalkyl group having 2 to 19 carbon atoms; as the (B-20), an aromatic hydrocarbon group or heteroaromatic group which is substituted with an alkyl amino group having 1 to 19 carbon atoms; as the (B-21), an aromatic hydrocarbon group or heteroaromatic group which is substituted with an alkyl amino alkyl group having 2 to 19 carbon atoms; and as the (B-22), an aromatic hydrocarbon group or heteroaromatic group which is substituted with an alkynyl group having 2 to 20 carbon atoms; are preferable.

In order to obtain a compound with higher mobility, as the (B-1), an unsubstituted aromatic hydrocarbon group or unsubstituted heteroaromatic group; as the (B-2), a halogenated aromatic hydrocarbon group or heteroaromatic group; as the (B-3), an aromatic hydrocarbon group or heteroaromatic group in which an aromatic hydrocarbon group or a heteroaromatic group is connected through a single bond; as the (B-5), an aromatic hydrocarbon group or heteroaromatic group which is substituted with a linear or branched alkyl group having 1 to 20 carbon atoms; as the (B-6), an aromatic hydrocarbon group or heteroaromatic group which is substituted with an alicyclic alkyl group having 1 to 20 carbon atoms; as the (B-7), an aromatic hydrocarbon group or heteroaromatic group which is substituted with an alkoxy group having 1 to 19 carbon atoms; and as the (B-8), an aromatic hydrocarbon group or heteroaromatic group which is substituted with an alkoxyalkyl group having 2 to 19 carbon atoms; are particularly preferable.

Specific examples of the (B-1) include an unsubstituted monocyclic or polycyclic aromatic hydrocarbon group having 6 to 24 carbon atoms such as a phenyl group, a naphthyl group, an azulenyl group, an acenaphthenyl group, an anthranyl group, a phenanthryl group, a naphthacenyl group, a fluorenyl group, a pyrenyl group, a chrysenyl group and a perylenyl group; an unsubstituted 5-membered or 6-membered heteroaromatic group, and a polycyclic heteroaromatic group in which the heteroaromatic group is condensed with another aromatic group, such as a pyrrolyl group, an indolyl group, a furyl group, a thienyl group, an imidazolyl group, a benzofuryl group, a triazolyl group, a benzotriazolyl group, a benzothienyl group, a pyrazolyl group, an indolizinyl group, a quinolinyl group, an isoquinolinyl group, a carbazolyl group, dibenzofuranyl group, a dibenzothiophenyl group, an indolinyl group, a triazolyl group, a pyridyl group, a pyrimidyl group, a pyrazinyl group, a pyridazinyl group, a thiadiazinyl group, an oxadiazolyl group, a benzoquinolinyl group, a thiadiazolyl group, a pyrrolothiazolyl group, a pyrrolopyridazinyl group, a tetrazolyl group and an oxazolyl group.

Specific examples of the (B-2) include a group obtained by substituting the aromatic hydrocarbon group or the heteroaromatic group with a halogeno group such as a fluoro group, a chloro group, a bromo group and an iodo group, such as a 4-fluorophenyl group, a 2,6-fluorophenyl group, a 4-chlorophenyl group, a 2,3,4,5,6-perfluorophenyl group, a fluoropyridinyl group and a fluoroindolyl group.

Specific examples of the (B-3) include a biphenyl group, a terphenyl group, a binaphthyl group, a bipyridyl group, a bithienyl group, a terthienyl group, a quaterthienyl group, a quinquethienyl group, a sexithienyl group, a furylphenyl group and a thienylphenyl group.

Specific examples of the (B-5) include a tolyl group, a xylyl group, an ethyl phenyl group, an n-propyl phenyl group, an isopropyl phenyl group, an n-butyl phenyl group, a tert-butyl phenyl group, an n-pentyl phenyl group, an n-hexyl phenyl group, an n-heptyl phenyl group, an n-octyl phenyl group, a 2-ethyl hexyl phenyl group, an n-decylphenyl group, a stearyl phenyl group, a 5-methyl thienyl group, a 5-hexyl thienyl group, a 5-decyltienyl group and a 5-stearyl thienyl group.

Specific examples of the (B-6) include a cyclohexyl phenyl group, a 4-methylcyclohexyl phenyl group and a 4-ethylcyclohexyl phenyl group.

Specific examples of the (B-7) include a methoxyphenyl group, an ethoxyphenyl group, a propoxyphenyl group, an isopropoxyphenyl group, a butoxyphenyl group, a pentyloxyphenyl group, a hexyloxyphenyl group, a heptyloxyphenyl group, an octyloxyphenyl group, a 2-ethylhexyloxyphenyl group, a decyloxyphenyl group, a dodecyloxyphenyl group and a stearyloxyphenyl group.

Specific examples of the (B-8) include a 4-(2-ethoxyethyl) phenyl group, a 4-(2-n-hexyloxyethyl) phenyl group, a 4-(2-n-heptyloxyethyl) phenyl group, a 4-(2-n-tetradecyloxyethyl) phenyl group, a 4-(2-cyclohexyloxyethyl) phenyl group, a 4-(12-ethoxododecyl) phenyl group, a 4-(cyclohexyloxyethyl) phenyl group, a 5-(2-ethoxyethyl) thienyl group, a 5-(2-n-tetradecyloxyethyl) thienyl group, a 5-(2-cyclohexyloxyethyl) thienyl group and a 5-(12-ethoxydodecyl) thienyl group.

Hereinafter, specific examples of the compound of the present invention will be described; however, the compound used in the present invention is not limited to the following examples.

[Chem. 10]

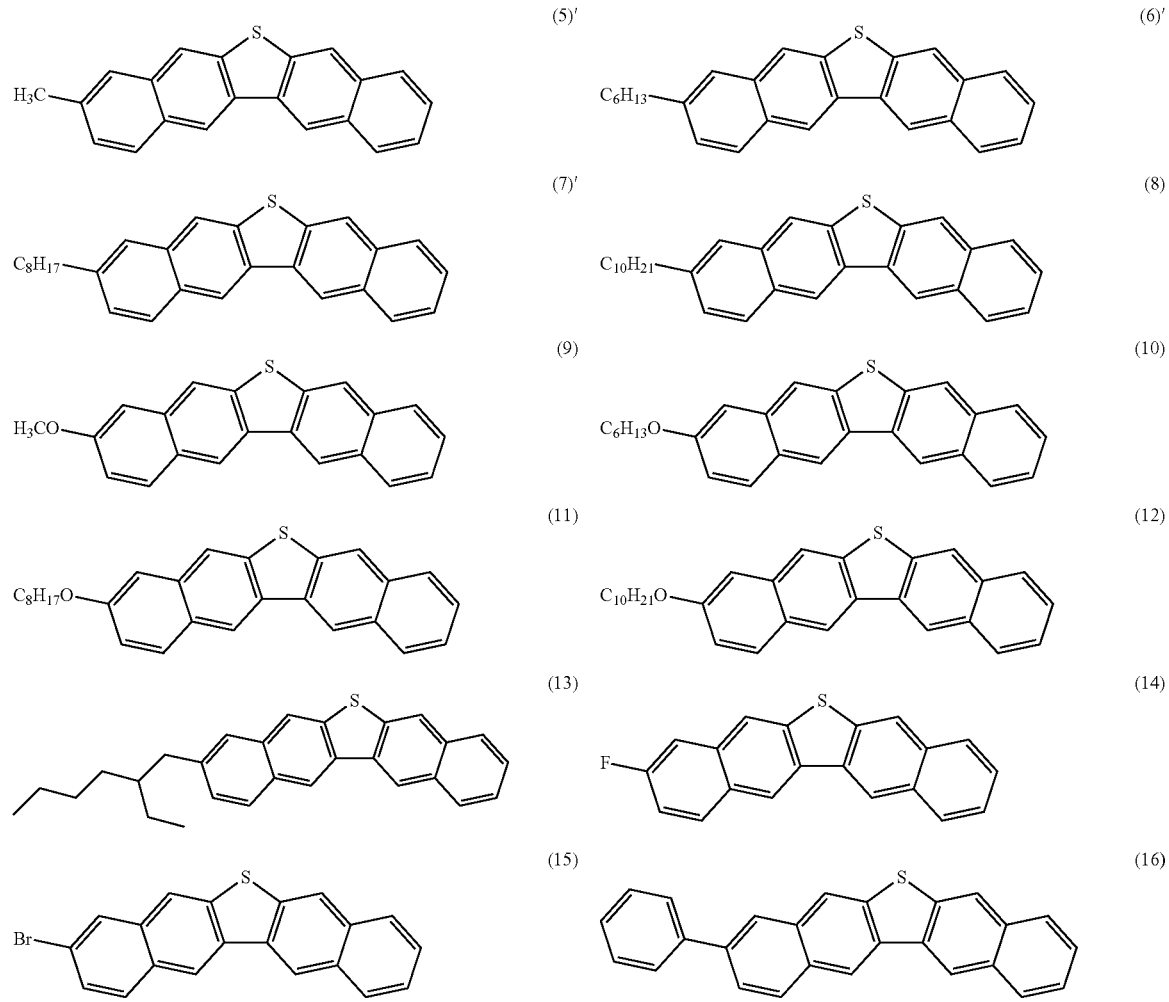

-continued
(17)
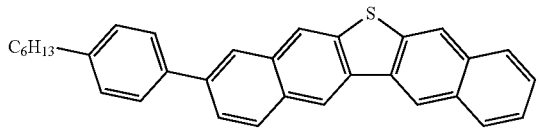
(18)
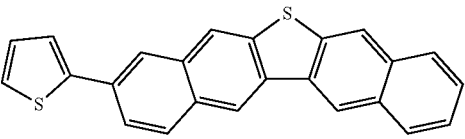
(19)
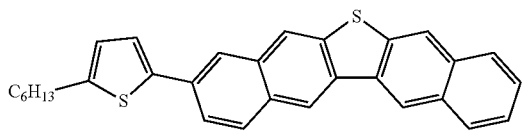
(20)
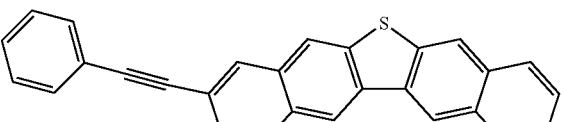
(21)
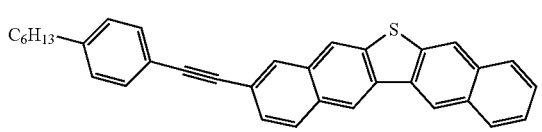
(22)
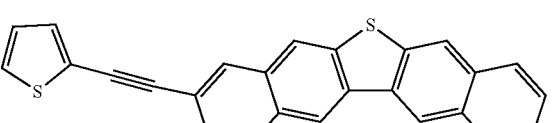
(23)
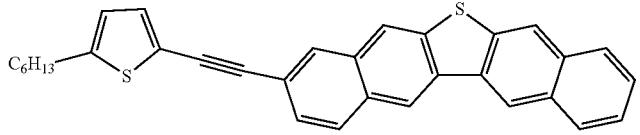
[Chem. 11]
(24)
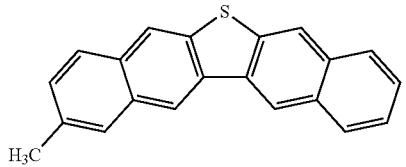
(25)
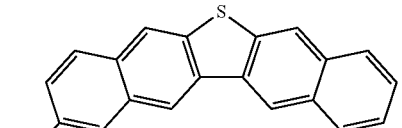
(26)
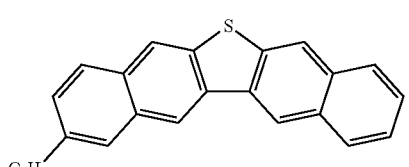
(27)
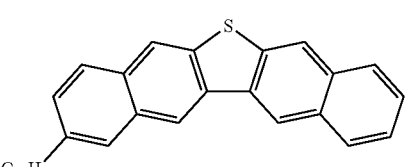
(28)
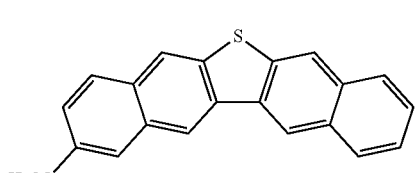
(29)
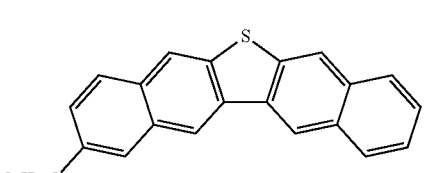
(30)
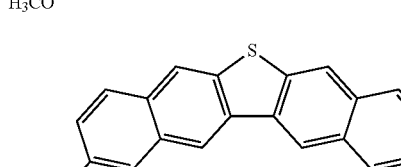
(31)
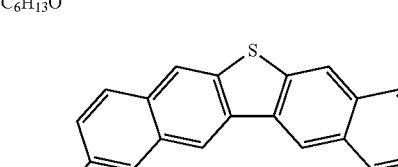
(32)
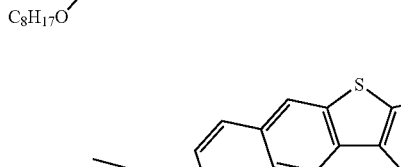
(33)
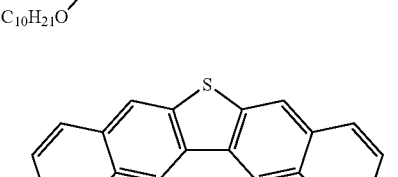

-continued
(34)
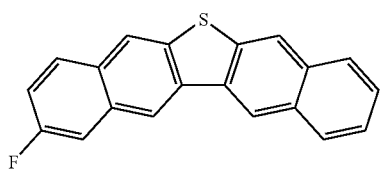
(35)
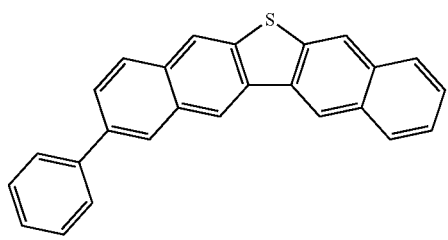
(36)
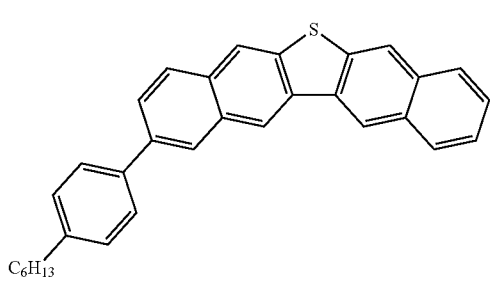
(37)
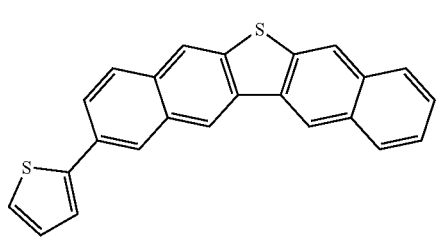
(38)
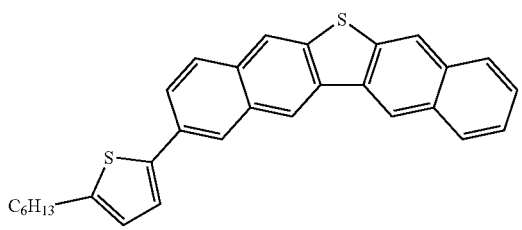
(39)
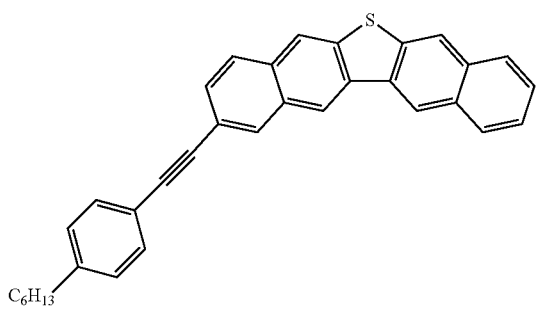
(40)
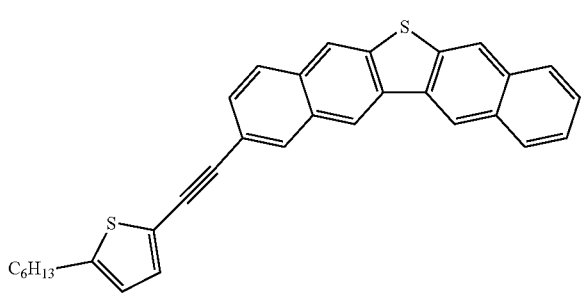
(41)
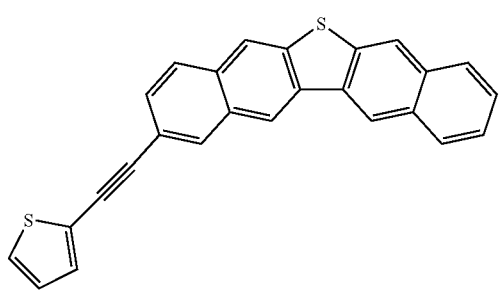
(42)
[Chem. 12]
(43)
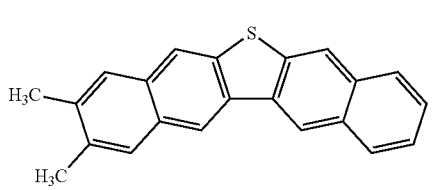
(44)
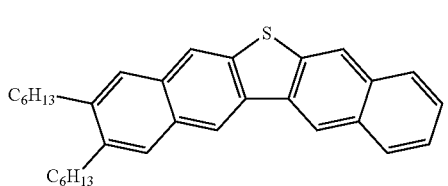

-continued
(45) 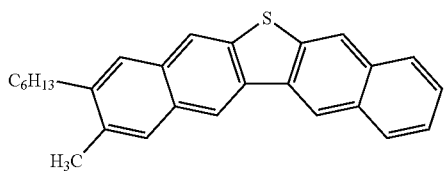
(46) 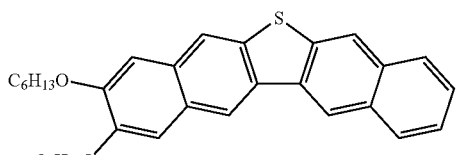
(47) 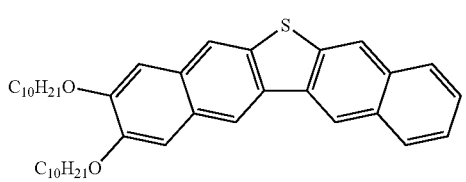
(48) 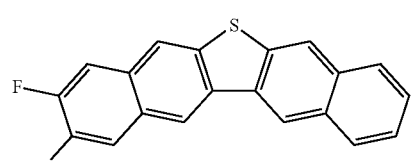
(49) 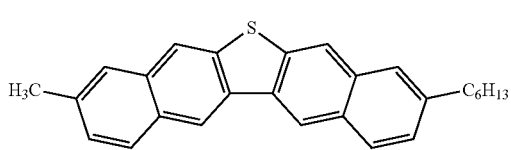
(50) 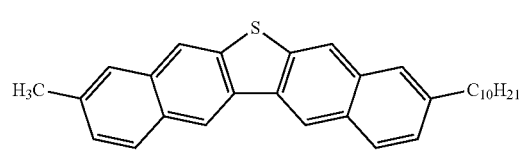
(51) 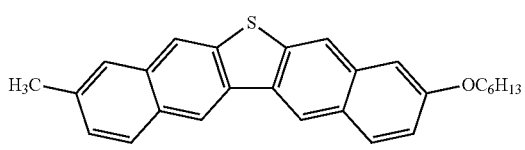
(52) 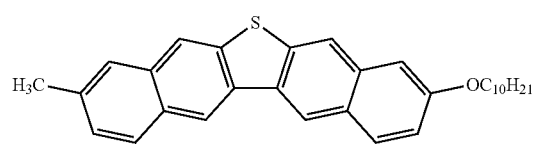
(53) 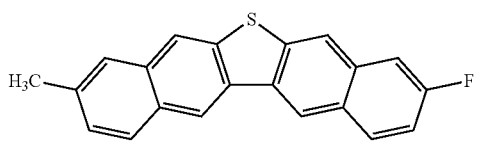
(54) 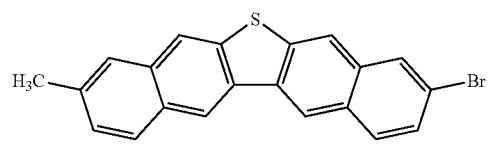
(55) 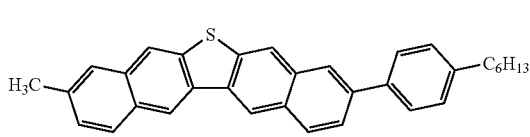
(56) 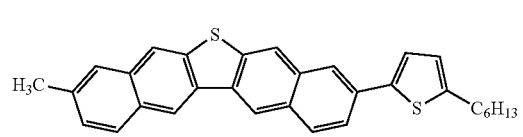
(57) 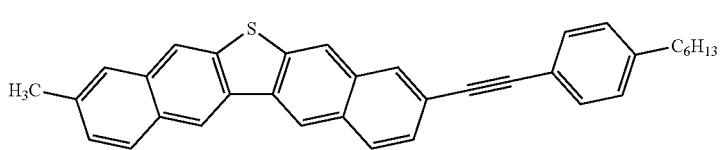
[Chem. 13]
(58) 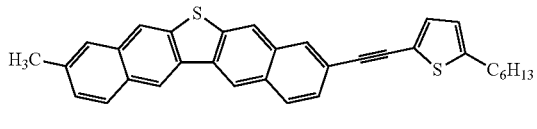
(59) 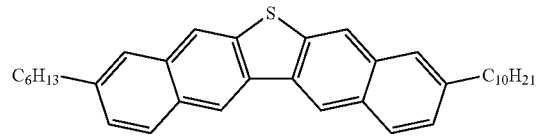
(60) 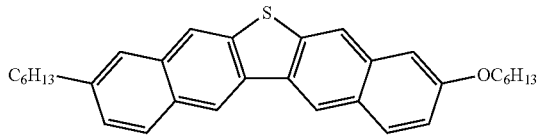
(61) 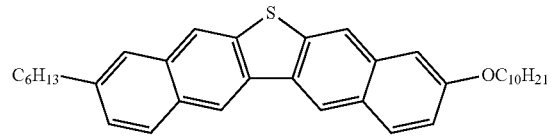

(62) 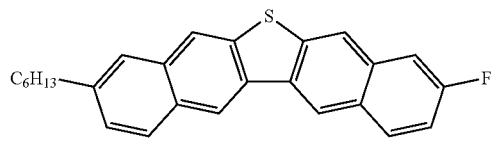
(63) 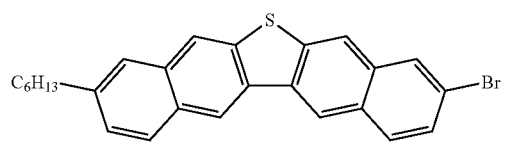
(64) 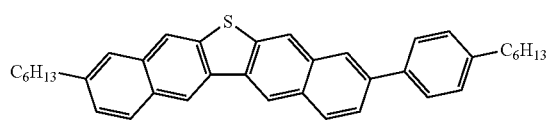
(65) 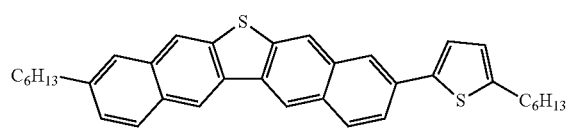
(66) 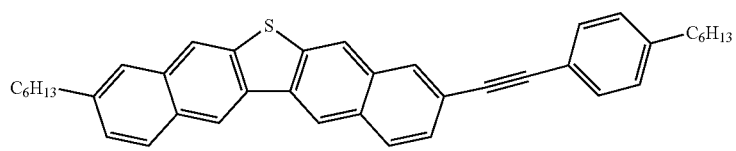
(67) 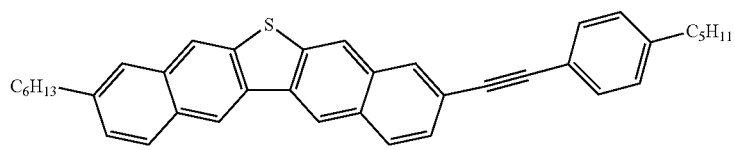
(68) 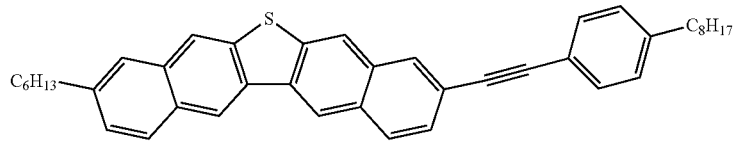
(69) 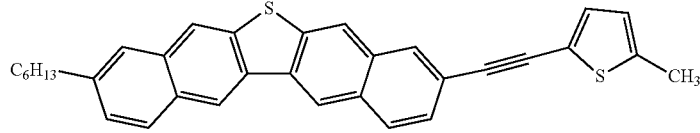
(70) 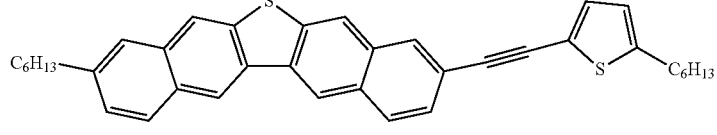
(71) 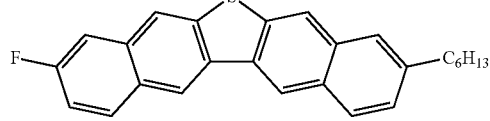
(72) 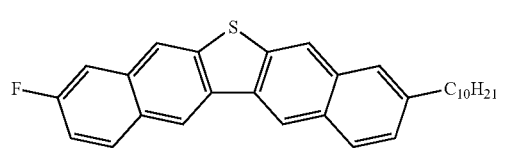
(73) 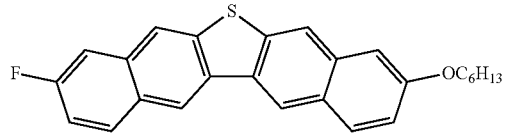
(74) 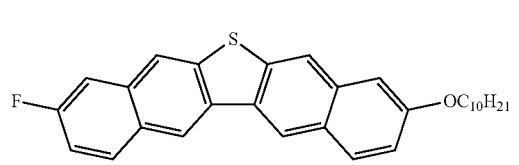
(75) 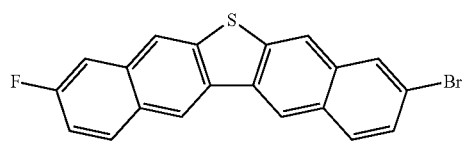

-continued
[Chem. 14]
(76)
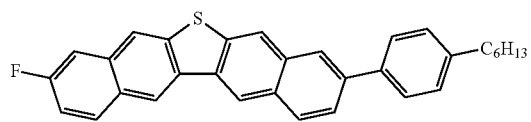
(77)
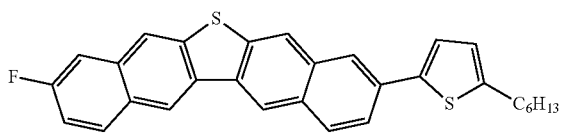
(78)
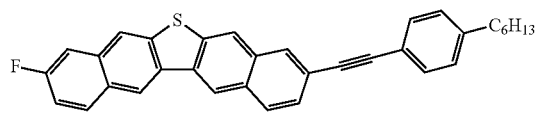
(79)
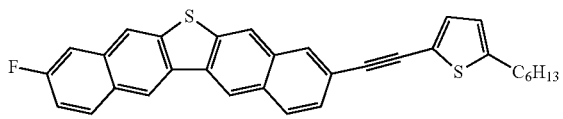
(80)
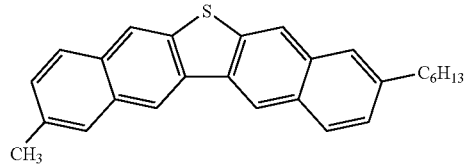
(81)
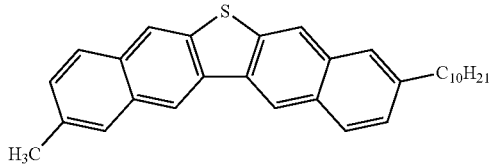
(82)
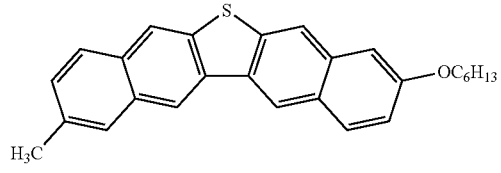
(83)
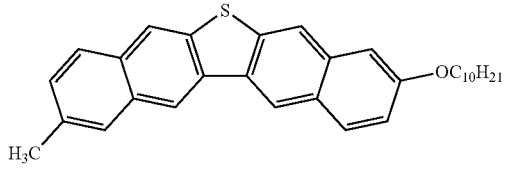
(84)
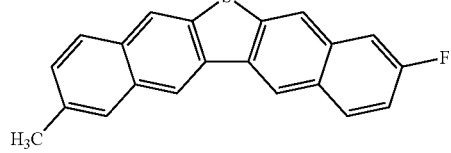
(85)
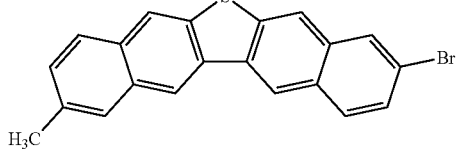
(86)
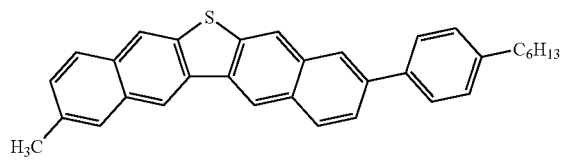
(87)
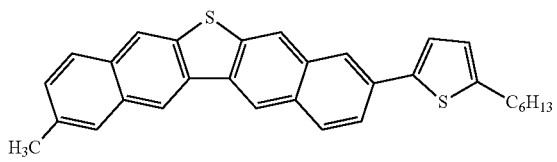
(88)
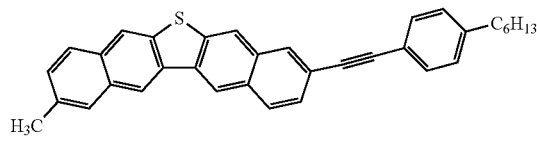
(89)
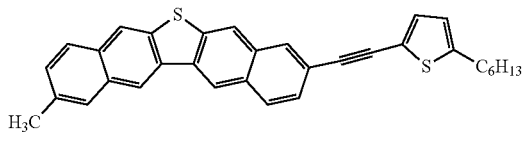
(90)
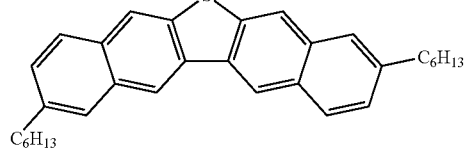
(91)
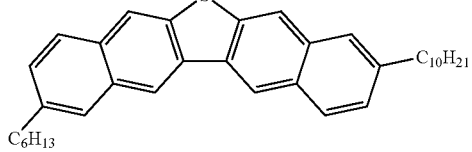
(92)
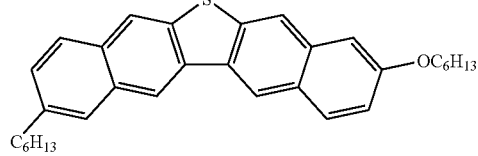
(93)
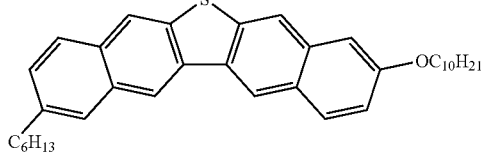

-continued
[Chem. 15]
(94) 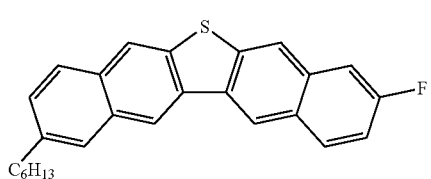
(95) 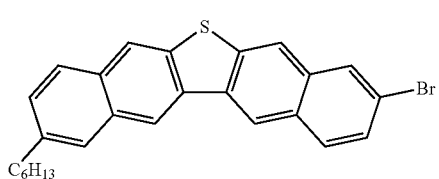
(96) 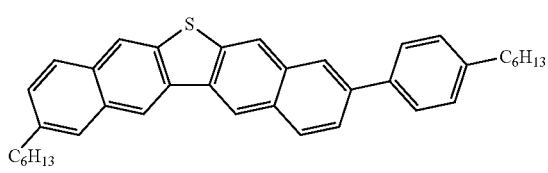
(97) 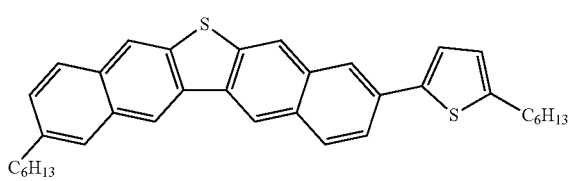
(98) 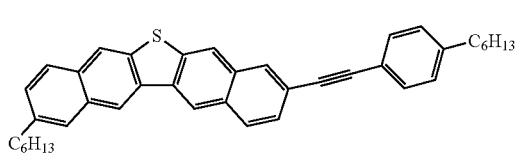
(99) 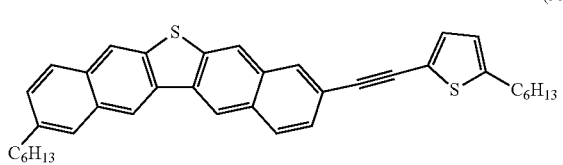
(100) 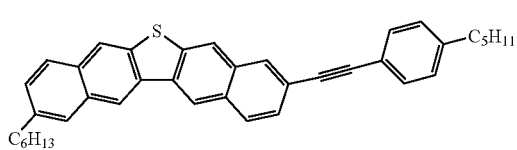
(101) 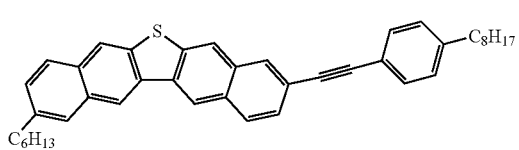
(102) 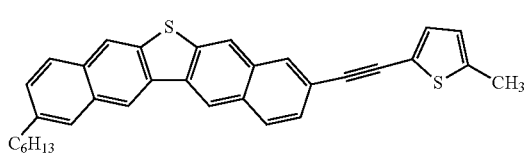
(103) 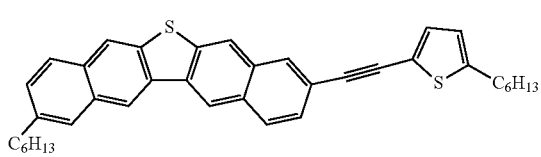
(104) 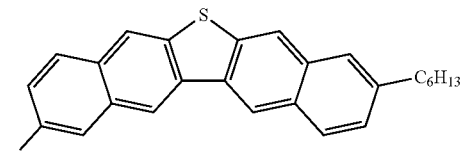
(105) 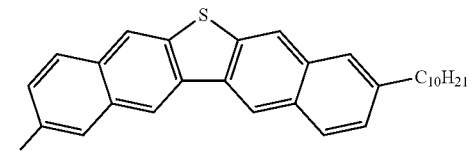
(106) 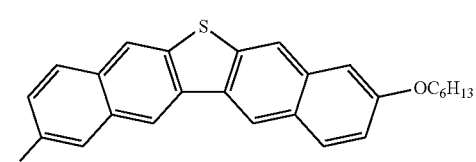
(107) 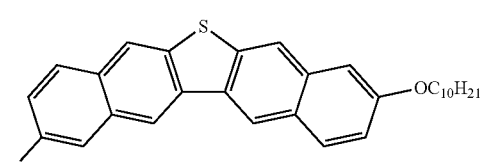
(108) 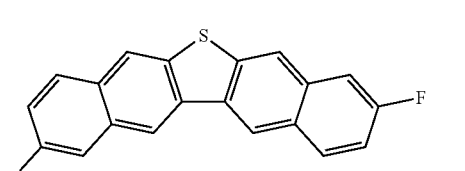
(109) 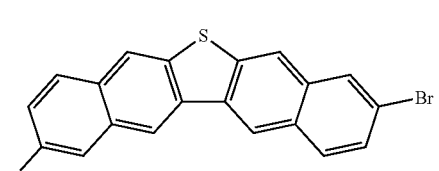

-continued
(110)
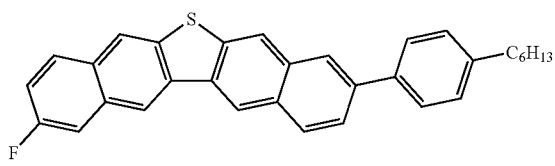
(111)
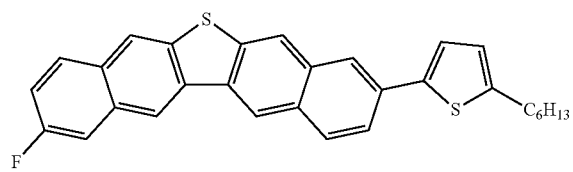
[Chem. 16]
(112)
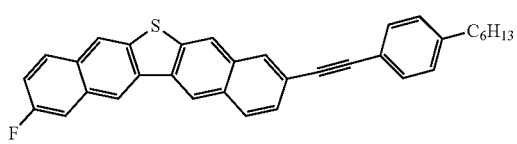
(113)
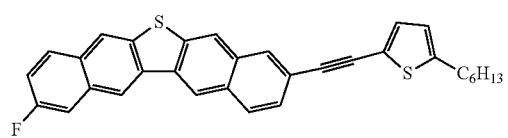
(114)
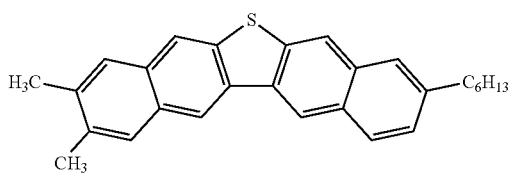
(115)
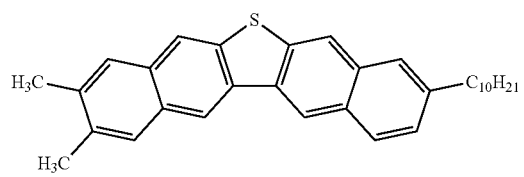
(116)
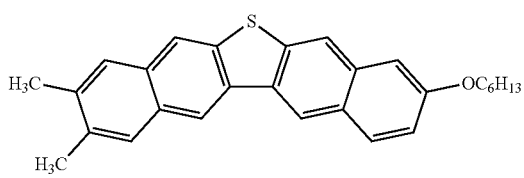
(117)
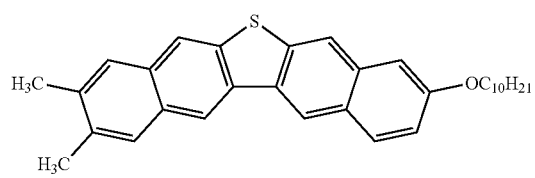
(118)
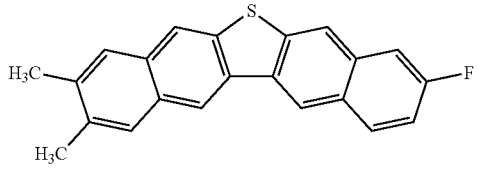
(119)
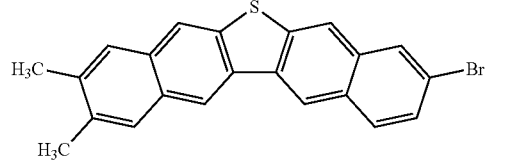
(120)
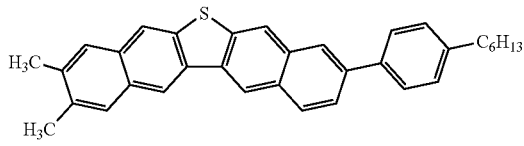
(121)
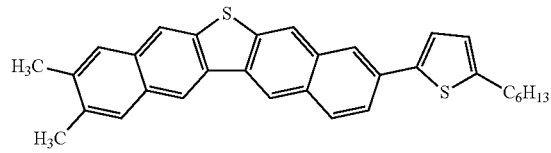
(122)
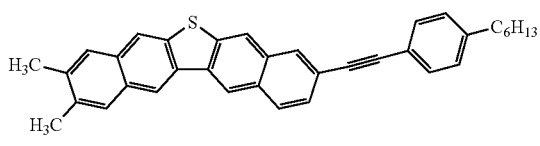
(123)
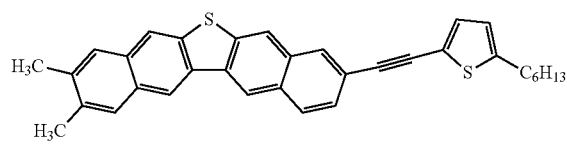
(124)
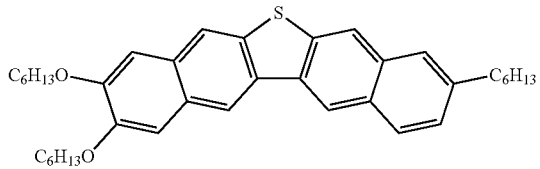
(125)
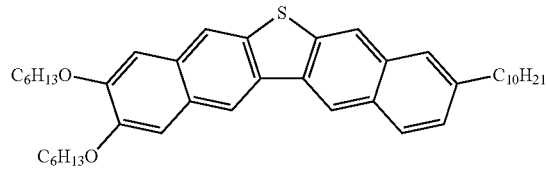

-continued
(126) 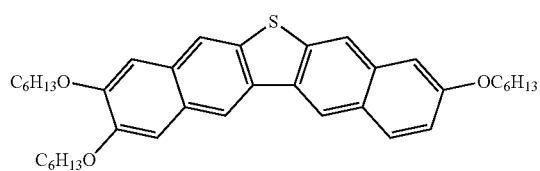
(127) 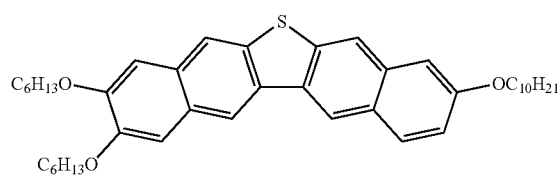
(128) 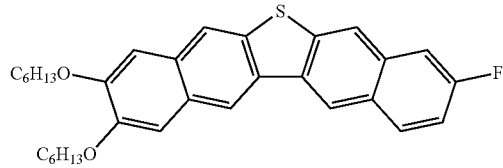
(129) 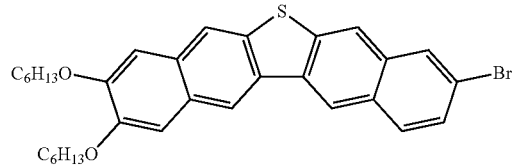
[Chem. 17]
(130) 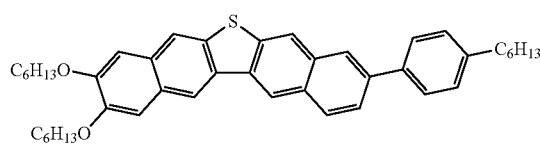
(131) 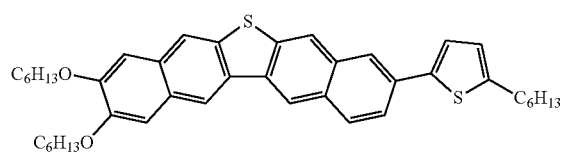
(132) 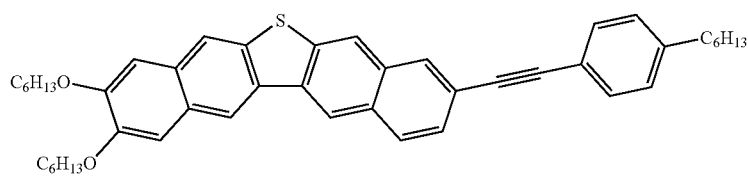
(133) 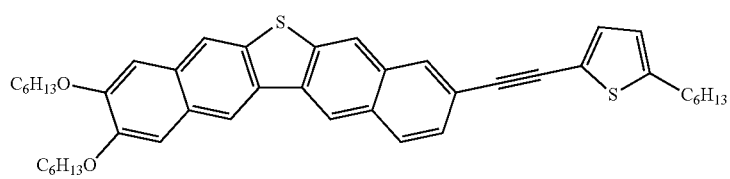
(134) 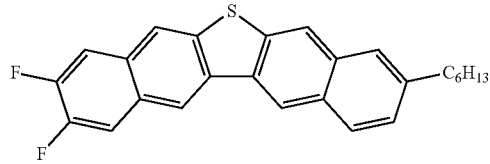
(135) 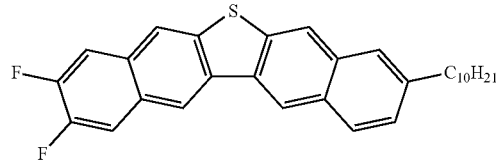
(136) 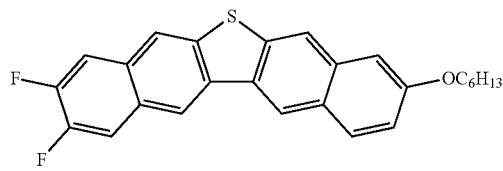
(137) 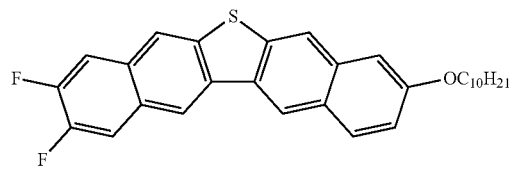
(138) 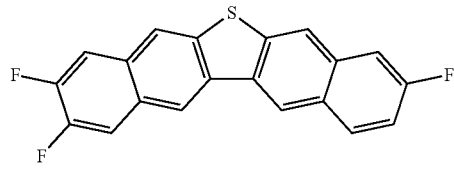
(139) 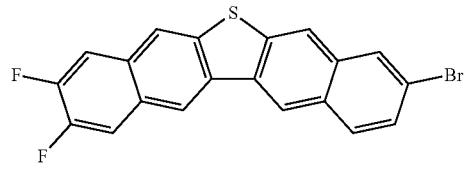

-continued
(140)
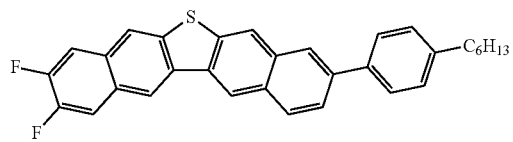
(141)
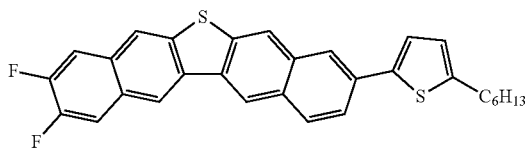
(142)
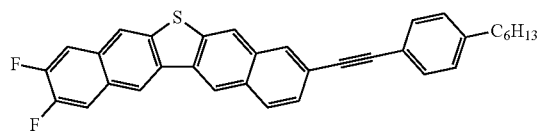
(143)
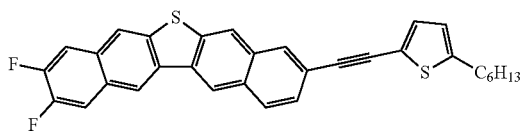
(144)
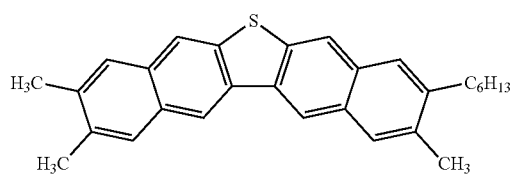
(145)
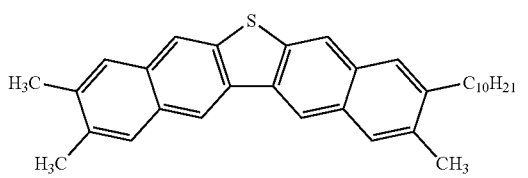
(146)
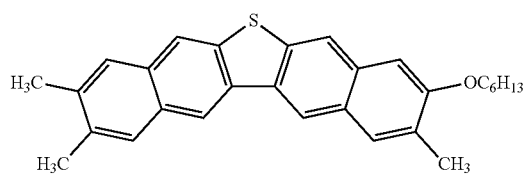
(147)
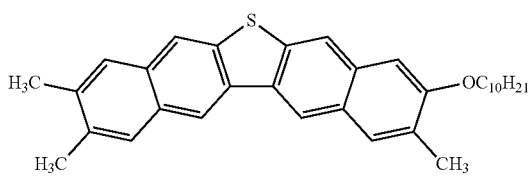
[Chem. 18]
(148)
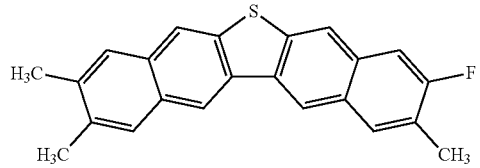
(149)
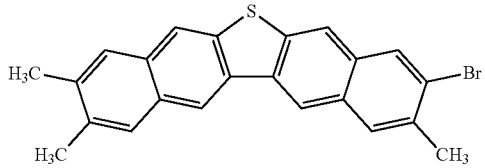
(150)
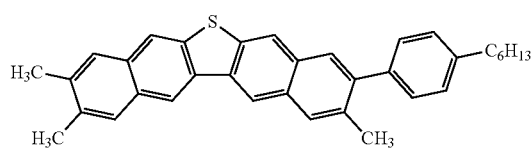
(151)
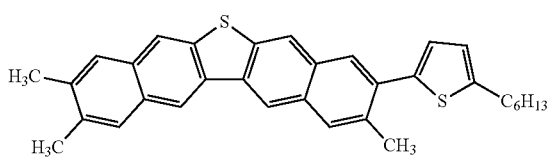
(152)
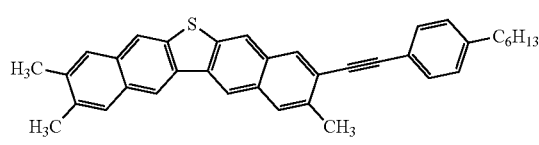
(153)
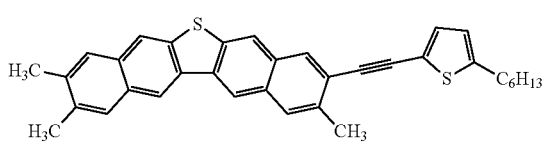
(154)
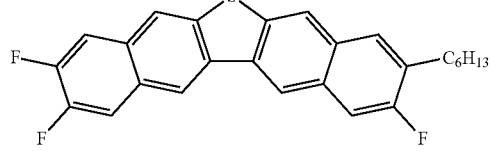
(155)
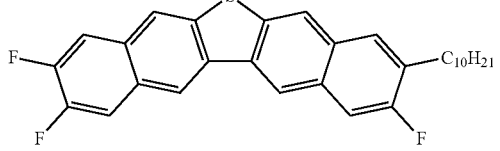

-continued
(156) 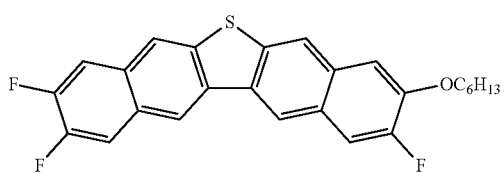
(157) 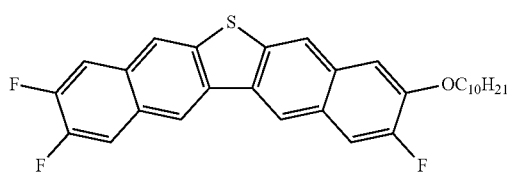
(158) 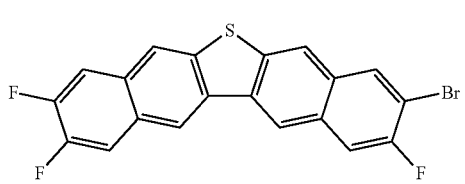
(159) 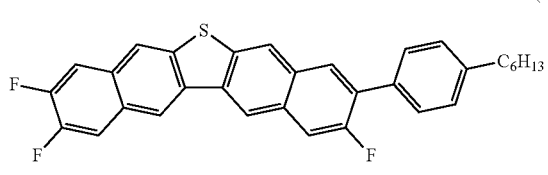
(160) 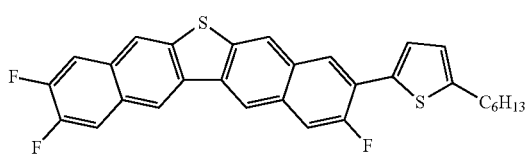
(161) 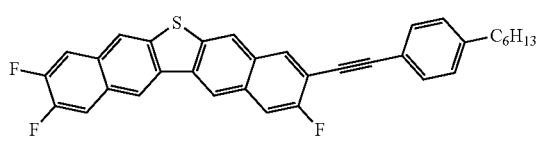
(162) 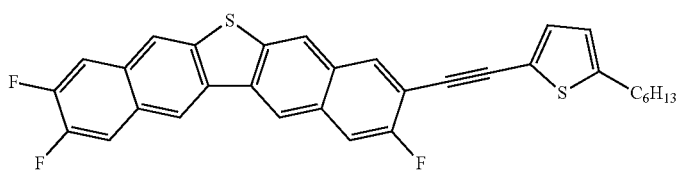
[Chem. 19]
(163) 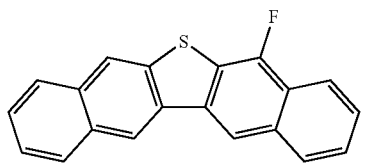
(164) 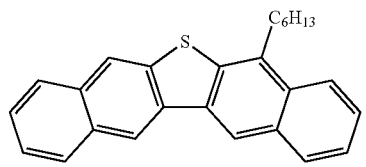
(165) 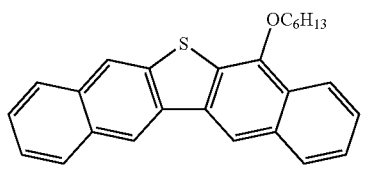
(166) 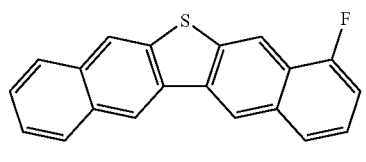
(167) 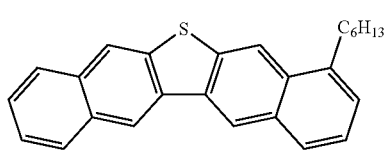
(168) 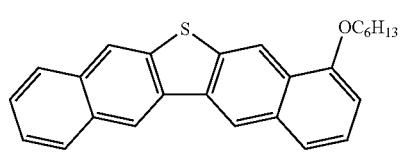
(169) 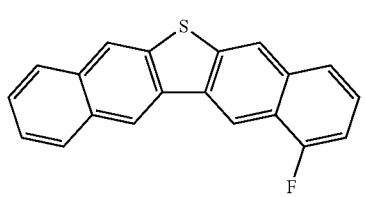
(170) 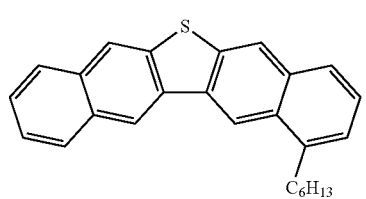

-continued

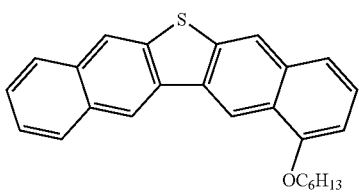 (171)

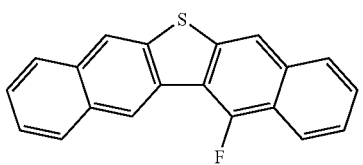 (172)

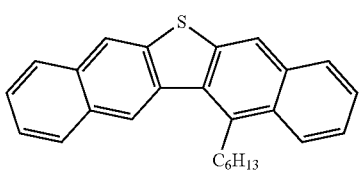 (173)

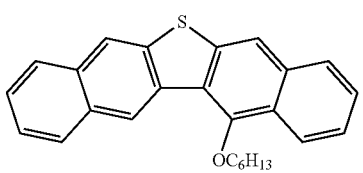 (174)

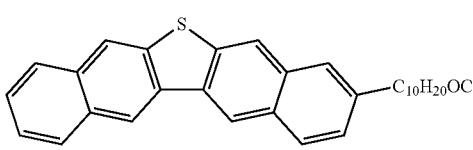 (175)

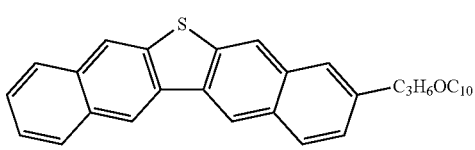 (176)

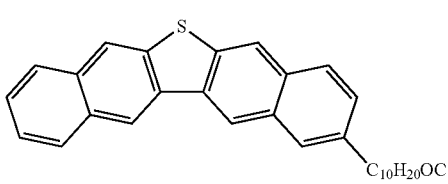 (177)

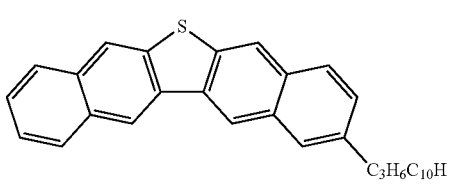 (178)

Organic Semiconductor Material and Ink

The compound of the present invention can be used as an organic semiconductor material for an organic semiconductor device. In order to use the compound of the present invention as an organic semiconductor, typically, the compound is used in a state of film morphology (organic semiconductor film or organic semiconductor layer). Regarding the film formation, it may be formed by a conventionally well-known dry film formation method such as vacuum deposition, but it is preferable to be formed by a wet film formation method (coating method or printing method) which is capable of forming a film at low temperature and is excellent productivity, and thus, the compound of the present invention, that is, the organic semiconductor material is preferably used as ink. The compound of the present invention is dissolved in a solvent to thereby prepare the ink. In addition, in order to impart ink properties (print suitability) to the extent that the semiconductor properties are not impaired, a leveling agent such as a fluorine-based or silicon-based leveling agent and a polymer compound such as polystyrene, an acrylic resin, or a high molecular weight organic semiconductor compound can also be added as a viscosity regulator.

Any solvent may be used, and two or more kinds of solvents may be used in combination. Specifically, an aliphatic solvent such as n-hexane, n-octane, n-decane, and n-dodecane can be exemplified.

Specific examples further include an alicyclic solvent such as cyclohexane; an aromatic solvent such as benzene, toluene, cumene, o-xylene, m-xylene, p-xylene, p-cymene, mesitylene, anisole, 2-methyl anisole, 3-methyl anisole, 4-methyl anisole, 2,5-dimethyl anisole, 3,5-dimethoxytoluene, 2,4-dimethyl anisole, phenetole, methyl benzoate, ethyl benzoate, propyl benzoate, butyl benzoate, 1,5-dimethyl tetralin, n-propyl benzene, n-butyl benzene, n-pentyl benzene, 1,3,5-triethylbenzene, 1,3-dimethoxybenzene, 2,5-diethoxybenzene, chlorobenzene, o-dichlorobenzene, and trichlorobenzene; an ether solvent such as tetrahydrofuran, dioxane, ethylene glycol diethyl ether, anisole, benzyl ethyl ether, ethyl phenyl ether, diphenyl ether, and methyl t-butyl ether; and an ester solvent such as methyl acetate, ethyl acetate, ethyl cellosolve, and propylene glycol methyl ether acetate; an alcoholic solvent such as methanol, ethanol, and isopropanol; a ketone solvent such as acetone, methyl ethyl ketone, cyclohexanone, 2-hexanone, 2-heptanone, and 3-heptanone; and other dimethyl formamide, dimethyl sulfoxide, and diethyl formamide; however, the compound of the invention is not limited thereto.

The concentration of the compound of the present invention in the prepared liquid composition is preferably in a range of 0.01% to 20% by weight, and is further preferably in a range of 0.1% to 10% by weight.

In addition, depending on the purpose, the organic semiconductor ink of the present invention may contain other organic semiconductor materials in addition to the compound of the present invention. That is, the organic semiconductor ink may contain an electron donating material, an electron accepting material, an electron transporting material, a hole transporting material, a light emitting material, a light absorbing material, and the like. Examples of such materials include a π-conjugated polymer exhibiting semiconductive properties, a non-π-conjugated polymer exhibiting semiconductive properties, and a low molecular weight organic semiconductor compound.

The organic semiconductor ink of the present invention contributes to a homogeneous organic semiconductor film with high orderly arrangement of molecular arrangement. Therefore, the obtained organic semiconductor film can exhibit high mobility. In addition, there is no need to perform special processing such as special printing film formation or thermal annealing in order to obtain a film with high orderly arrangement of molecular arrangement and it is possible to obtain an organic semiconductor film with high mobility only by adding dropwise and drying the ink.

Organic Semiconductor Device

Next, the organic semiconductor device of the present invention will be described. The organic semiconductor device of the present invention is an organic semiconductor device containing the compound of the present invention in an active layer portion (semiconductor layer).

Examples of the organic semiconductor device include a diode; a memory; a photoelectric conversion device such as a photodiode, a solar cell, a light receiving element; a transistor such as a field effect transistor, a static induction transistor, and a bipolar transistor; a light emitting device such as an organic EL and a light emitting transistor; sensors such as a temperature sensor, a chemical sensor, a gas sensor, a humidity sensor, a radiation sensor, a biosensor, a blood sensor, an immunosensor, an artificial retina, a taste sensor, and a pressure sensor; and a logic circuit unit such as RFID. However, the organic semiconductor device is not limited these examples.

Among them, the compound of the present invention has high mobility equal to or greater than 1 $cm^2/Vs$ as an organic semiconductor material, and thus application to the organic transistor or the light emitting device is particularly useful.

Organic Transistor

Next, an organic transistor containing the compound of the present invention will be described.

The organic transistor is typically configured to include a source electrode, a drain electrode, agate electrode, a gate insulating layer, and an organic semiconductor layer, and there are various kinds of organic transistors depending on the disposition of each electrode and each layer. However, the compound of the present invention and the organic semiconductor material are not limited to the kinds of the organic transistors, and can be used for any organic transistor. Regarding the kinds of the organic transistors, it is possible to refer to Material Science of Aldrich, Basics, 6, "Basics of organic transistor" and the like.

As one example, a bottom gate bottom contact type illustrated in FIG. 1 will be described in detail. Reference 1 is a substrate, reference 2 is a gate electrode, reference 3 is a gate insulating layer, reference 4 is an organic semiconductor layer, reference 5 is a source electrode, and reference 6 is a drain electrode.

Here, the bottom gate bottom contact type (hereinafter, BC type) has more practical structure from the aspect that the organic semiconductor material which is more deteriorated than other element forming materials (metal for electrode material and resin for gate insulating material) regarding heat resistance, weather resistance, and solvent resistance is treated at last step of the element producing process. On the other hand, as compared with a bottom gate top contact type (hereinafter, TC type), the BC type tends to be deteriorated in the element properties (Material Science of Aldrich, Basics, 6, Chapter 2.2 "Basics of organic transistor").

The features of the compound of the present invention is that even if conventionally well-known compounds for organic semiconductor material exhibit high properties in the TC type, but the properties are not realized in the BC type; whereas, as described below, even in the BC type, it has high mobility equal to or greater than 1 $cm^2/Vs$. The reason for this is that the compound of the present invention forms a polycrystalline film that contributes to high mobility with appropriate cohesive force only by adding dropwise and drying the ink droplets.

As the substrate, glass or a resin can be used, and in order to obtain a flexible TFT, a glass sheet, a resin sheet, and a plastic film can be used. Among them, the resin sheet and the plastic film are preferably used, from the aspect that weight reduction can be achieved in addition to flexibility, portability can be enhanced, and resistance to impact can be improved. Examples of the material include polyethylene terephthalate (PET), polyethylene naphthalate (PEN), polyether sulfone (PES), polyether imide, polyether ether ketone, polyphenylene sulfide, polyarylate, polyimide, polycarbonate (PC), cellulose triacetate (TAC), and cellulose acetate propionate (CAP).

The electrode materials of the gate electrode, the source electrode, and the drain electrode are not particularly limited as long as they are conductive materials, and examples thereof include platinum, gold, silver, nickel, chromium, copper, iron, tin, tin oxide, antimony, indium tin oxide (ITO), fluorine doped zinc oxide, carbon, graphite, glassy carbon, silver paste, carbon paste, lithium, beryllium, sodium, magnesium, potassium, calcium, scandium, titanium, manganese, zirconium, gallium, niobium, sodium, a sodium-potassium alloy, magnesium, lithium, aluminum, a magnesium/copper mixture, a magnesium/silver mixture, a magnesium/aluminum mixture, a magnesium/indium mixture, an aluminum/aluminum oxide mixture, and a lithium/aluminum mixture. Further, a conventionally well-known conductive polymer having improved conductivity by doping, for example, conductive polyaniline, conductive polypyrrole, conductive polythiophene, and a complex (PEDOT/PSS) of polyethylene dioxythiophene and a polystyrene sulfonic acid can be preferably used.

Examples of the method of forming an electrode include a method of patterning a conductive thin film which is formed according to a method of depositing and sputtering the above-described material as a raw material to thereby form an electrode according to conventionally well-known photolithography and a lift-off method, and a method of patterning a resist on the conductive thin film by thermal transfer or inkjet, and then etching the resist. A solution or the dispersion liquid of the conductive polymer, the dispersion liquid of conductive fine particles may be directly patterned by ink jet, the solution or dispersion liquid of a conductive polymer, or the dispersion liquid or a paste of the conductive fine particles may be applied to the film so as to form a coated film, and the obtained coated film may be patterned through lithography or laser ablation. Further, it is possible to employ a method of patterning the solution or dispersion liquid of the conductive polymer, or the dispersion liquid or the paste of the conductive fine particles according to various printing methods such as a screen printing method, an offset printing method, a gravure offset printing method, a letterpress printing method, a letterpress reversal printing method, and a microcontact printing method.

As the gate insulating layer, an organic thin film made of a thermoplastic resin such as polyparaxylylene, polystyrene, an acrylic resin, and a polyester resin; a thermosetting resin such as an epoxy resin, a urethane resin, a phenol resin, an unsaturated polyester resin, an alkyd resin, and a melamine resin; and a UV curable resin can be preferably used, and further, an inorganic thin film made of a silicon oxide film or the like can also be used.

The gate insulating layer can be produced by conventionally well-known wet film formation methods such as a spin coating method, a drop casting method, a cast coating method, a dipping method, a die coating method, a doctor blade method, a wire bar coating method, a bar coating method, a reverse coating method, an air doctor coating method, a blade coating method, an air knife coating method, a roll coating method, a squeeze coating method, an impregnation coating method, a transfer roll coating method, a kiss coating method, a slit coating method, a spray coating method, an electrostatic coating method, an ultrasonic spray coating method, a dispensing method, an ink jet method, a screen printing method, a gravure printing method, an offset printing method, a gravure offset printing method, a letterpress printing method, a letterpress reversal printing method, and a microcontact printing method, and may be patterned in a shape required by photolithography, if necessary.

The organic semiconductor layer can be formed into a film by using the compound of the present invention according to a conventionally well-known dry film formation method such as vacuum deposition method, but is preferably formed into a film by using the ink of the present invention according to a wet film formation method such as printing. The film thickness of the organic semiconductor layer is not particularly limited, but is typically in a range of 0.5 nm to 1 μm, and is preferably in a range of 2 nm to 250 nm.

Alternatively, for the purpose of improving crystallinity and improving the semiconductor properties, the organic semiconductor layer may be subjected to annealing after film formation if necessary. The temperature at the time of annealing is preferably in a range of 50° C. to 200° C., and is further preferably in a range of 70° C. to 200° C., the time is preferably in a range of 10 minutes to 12 hours, is further preferably in a range of 1 hour to 10 hours, and is still further preferably in a range of 30 minutes to 10 hours.

Examples of the film formation method include conventionally well-known wet film formation methods such as a spin coating method, a drop casting method, a cast coating method, a dipping method, a die coating method, a doctor blade method, a wire bar coating method, a bar coating method, a reverse coating method, an air doctor coating method, a blade coating method, an air knife coating method, a roll coating method, a squeeze coating method, an impregnation coating method, a transfer roll coating method, a kiss coating method, a slit coating method, a spray coating method, an electrostatic coating method, an ultrasonic spray coating method, a dispensing method, an ink jet method, a screen printing method, a gravure printing method, an offset printing method, a gravure offset printing method, a letterpress printing method, a letterpress reversal printing method, and a microcontact printing method.

The organic transistor of the present invention can be preferably used as a switching transistor of the pixels of a display device, a signal driver circuit element, a memory circuit element, and a signal processing circuit element. Examples of the display device include a liquid crystal display device, a dispersion type liquid crystal display device, an electrophoretic display device, a particle rotation display element, an electrochromic display device, an organic EL display device, and an electronic paper.

EXAMPLES

Hereinafter, the present invention will be described in more detail with reference to Examples, but the present invention is not limited thereto.

Example 1

Production of Compound (1)

[Chem. 20]

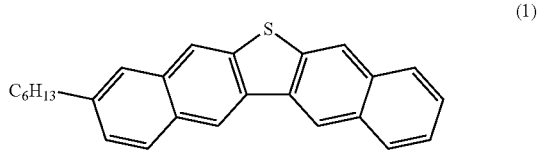

(1)

[Chem. 21]

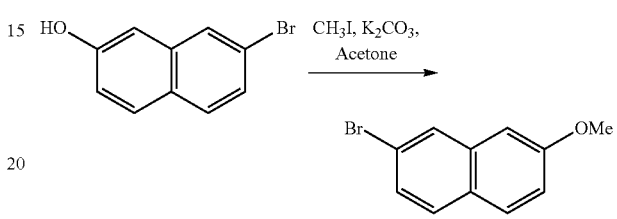

Under the argon atmosphere, 500 mL of dry acetone was added to 80.0 g (359 mmol) of 2-bromo-7-hydroxynaphthalene and 149 g (1.08 mol) of potassium carbonate, and the mixture was stirred at room temperature. After 44.9 mL (720 mmol) of iodomethane was added dropwise to the mixture, and then refluxed for two hours. The reaction mixture was cooled to room temperature, and 250 mL of water was added thereto. Acetone was distilled off under the reduced pressure, 750 mL of water was further added thereto, and the mixture was stirred for 10 minutes. The generated white precipitate was filtered and the filtrate was washed with 1.5 L of water. The obtained white solid is dried to thereby obtain 71.8 g of 2-bromo-7-methoxynaphthalene (yield, 84.4%).

$^1$H NMR (300 MHz, CDCl$_3$): δ7.89 (d, J=Hz, 1H), δ7.69 (d, J=9.3 Hz, 1H), δ7.62 (s, J=9.0 Hz, 6H), δ7.40 (dd, J=1.8 Hz, 8.4 Hz, 1H), δ7.14 (dd, J=2.4 Hz, 9.0 Hz, 1H), δ7.02 (s, J=2.4 Hz, 1H)

[Chem. 22]

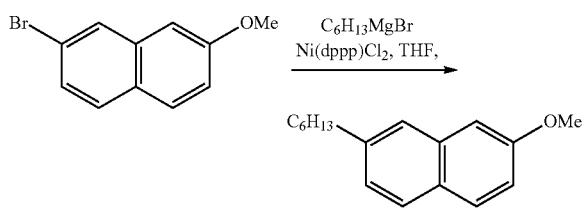

Under the argon atmosphere, 20 mL of dry tetrahydrofuran was added to 5.42 g (21.1 mmol) of 2-bromo-7-methoxynaphthalene, and 0.259 g (1.05 mmol) of dichloro[1,3-bis(diphenylphosphino)propane] nickel (II), and the mixture was stirred at −78° C. 11.6 mL (23.2 mmol) of 2 M ether solution of n-hexyl magnesium bromide was added dropwise to the reaction solution, and the temperature was slowly raised to room temperature. After refluxing for one hour, the reaction solution was cooled to room temperature. After 5 mL of water was slowly added dropwise to the reaction solution, the solid content was removed by celite filtration. The filtrate was dried by magnesium sulfate and the solvent was distilled off. The obtained crude product was separated and purified by silica gel column chromatography (hexane/chloroform 7/3), and thereby 4.55 g of 2-hexyl-7-methoxynaphthalene (yield, 82.1%) was obtained.

$^1$H NMR (300 MHz, CDCl$_3$): δ7.70-7.67 (m, 2H), δ7.51 (s, 1H), δ7.20-7.17 (m, 1H), δ7.08-7.06 (m, 2H), δ3.91 (s, 3H), δ2.74 (t, J=7.5 Hz, 3H), δ1.75-1.64 (m, 2H), δ1.42-1.24 (m, 6H), δ0.93-0.86 (m, 3H)

[Chem. 23]

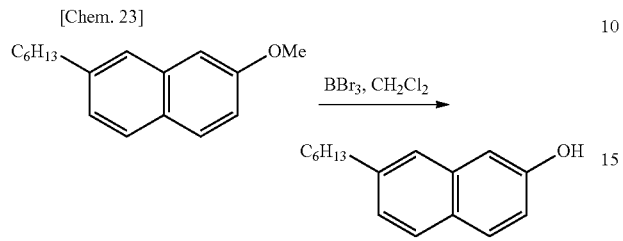

Under the argon atmosphere, 20 mL of dry dichloromethane was added to 4.00 g (16.5 mmol) of 2-hexyl-7-methoxynaphthalene, and the mixture was stirred at −78° C. 28 mL (28 mmol) of 1 M dichloromethane solution of boron tribromide was added dropwise to the reaction solution, then, the temperature was raised to room temperature and the reaction solution was stirred for one hour. The reaction was stopped by adding water to the reaction solution which is cooled again to −78° C. 250 mL of CH$_2$Cl$_2$ added to a reaction solution, and after washing with water, an organic phase was dried with magnesium sulfate and a solvent was distilled off, thereby obtaining 3.53 g (yield, 91.8%) of 2-hexyl-7-hydroxynaphthalene.

$^1$H NMR (300 MHz, CDCl$_3$): δ7.71-7.66 (m, 2H), δ7.44 (s, 1H), δ7.17 (dd, J=1.5 Hz, 8.4 Hz, 1H), δ7.08 (d, J=2.7 Hz, 1H), δ7.02 (dd, J=2.7 Hz, 8.7 Hz, 1H), δ4.20-4.00 (br, 1H), δ3.80 (s, 3H), δ2.73 (s, J=7.5 Hz, 2H), δ1.68-1.62 (m, 2H), δ1.41-1.22 (m, 6H), δ0.90-0.86 (m, 3H)

[Chem. 24]

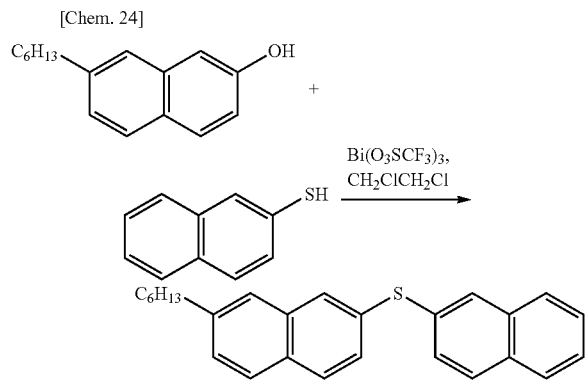

Under the argon atmosphere, 8.8 mL of 1,2-dichloroethane was added to 1.00 g (4.38 mmol) of 2-hexyl-7-hydroxynaphthalene, 0.701 g (4.38 mmol) of 2-naphthalenethiol, and 0.144 g (0.219 mmol) of bismuth (III) trifluoromethane sulfonate, and the mixture was stirred at 80° C. for 16 hours. The reaction solution was concentrated, and the resultant crude product was separated and purified by silica gel column chromatography (cyclohexane), and thereby 1.36 g of 7-hexyl-2,2'-binaphthyl sulfide (yield, 83.8%) was obtained.

$^1$H NMR (300 MHz, CDCl$_3$): δ7.85-7.72 (m, 7H), δ7.47-7.23 (m, 6H), δ2.74 (t, J=7.4 Hz, 2H), δ1.70-1.63 (m, 2H), δ1.38-1.28 (m, 6H), δ0.88 (t, J=6.9 Hz, 3H)

[Chem. 25]

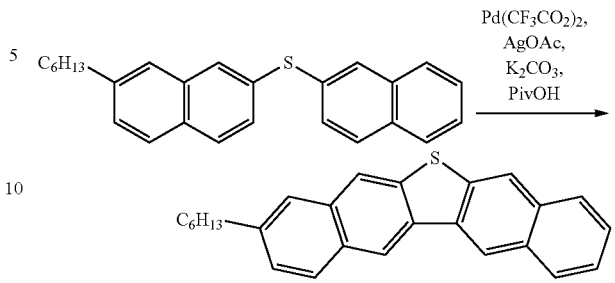

0.500 g (1.35 mmol) of 7-hexyl-2,2'-binaphthyl sulfide, 0.0449 g (0.135 mmol) of palladium (II) trifluoroacetate, 0.901 g (5.40 mmol) of silver acetate, and 0.187 g (1.35 mmol) of potassium carbonate were added to 2.7 mL of pivalic acid, and the mixture was stirred at 110° C. for 16 hours. The reaction solution was diluted with chloroform and filtered through celite. The filtrate is concentrated, the obtained crude product is separated and purified by silica gel column chromatography (hexane), and thereby a 0.280 mg 3-hexyl dinaphtho[2,3-b:2',3'-d]thiophene (yield, 55.9%) which is a compound (1) was obtained.

$^1$H NMR (300 MHz, CDCl$_3$): δ8.70 (s, 1H), δ8.68 (s, 1H), δ8.22 (s, 1H), δ8.15 (s, 1H), δ8.06-8.03 (m, 1H), δ7.98-7.96 (m, 1H), δ7.92-7.89 (m, 1H), δ7.67 (s, 1H), δ7.54-7.51 (m, 2H), δ7.38 (dd, J=1.5 Hz, 8.4 Hz, 1H), δ2.82 (t, J=7.2 Hz, 2H), δ1.76-1.70 (m, 2H), δ1.36-1.24 (m, 6H), δ0.90 (t, J=6.6 Hz, 3H)

Production of Organic Transistor

Aluminum having a thickness of about 30 nm was formed into a film on a glass substrate (corresponding to 1 in FIG. 1) by using a metal mask to form a gate electrode (corresponding to 2 in FIG. 1) according to a vacuum deposition method. Then, a poly(p-chloroxylylene) (Parylene C) thin film (the thickness of 500 nm) (corresponding to 3 of FIG. 1) was produced with dichloro-diparaxylylene (DPX-C, manufactured by Specialty Coating Systems, Inc.) as a raw material by using a parylene vapor deposition apparatus (Lab Coater PDS 2010, manufactured by Specialty Coating Systems, Inc.) according to a chemical vapor deposition (CVD) method. Further, source and drain electrodes made of gold thin film (the thickness of 40 nm) were patterned (corresponding to 5 and 6 of FIG. 1. A channel length L (a gap between the source electrode and the drain electrode) was set to be 75 μm, and a channel width W was set to be 5.0 mm) according to the vacuum deposition method. Next, a substrate obtained as described above was dip into 0.1% of ethanol solution of pentafluorothiophenol for one hour, and was dried by blowing nitrogen, then, 0.1 μL of liquid droplet of 0.4% p-xylene solution (organic semiconductor ink) of the compound (1) was drop-casted (dropped) between the source electrode and the drain electrode, and dried by natural concentration to thereby form an organic semiconductor layer (corresponding to 4 of FIG. 1) made of the compound (1) (organic semiconductor solution (ink) liquid droplet was drop-casted and dried to thereby form an organic semiconductor layer).

Evaluation of Semiconductor Properties (Mobility)

Regarding the organic transistor obtained as described above, the semiconductor properties (mobility) was evaluated. In a state where a source electrode was grounded, and −80 V of voltage was applied to a drain electrode, a current ($I_d$) flowing into the drain electrode was measured while sweeping the applied voltage ($V_g$) in a range of 0 to −80 V with respect to a gate electrode, by using a digital multimeter (SMU237, manufactured by Keithley), and thereby the semiconductor properties (mobility) were calculated from the slope of $\sqrt{I_d}$–$V_g$ based on (Equation 1). A unit is cm²/V·s.

[Equation 1]

$$I_d = (W/2L) \cdot C \cdot \mu \cdot (V_g - V_T)^2 \quad \text{(Equation 1)}$$

In the formula, W represents a channel width, L represents a channel length, μ represents mobility, C represents an electrical capacity per unit area of a gate insulating layer, and $V_T$ represents the threshold voltage.

The evaluation results are indicated in Table 1.

Example 2

Production of Compound (2)

[Chem. 26]

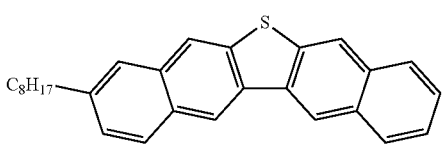

(2)

A compound (2) (yield, 64.3%) was obtained in accordance with Example 1 except that n-hexyl magnesium bromide was changed to n-octyl magnesium bromide in Example 1.

¹H NMR (300 MHz, CDCl₃): δ8.69 (s, 1H), δ8.67 (s, 1H), δ8.21 (s, 1H), δ8.14 (s, 1H), δ8.09-8.04 (m, 1H), δ8.03-7.98 (m, 1H), δ7.91-7.89 (m, 1H), δ7.66 (s, 1H), δ7.56-7.48 (m, 2H), δ7.38 (dd, J=1.5 Hz, 8.4 Hz, 1H), δ2.82 (t, J=7.2 Hz, 2H), δ1.77-1.69 (m, 2H), δ1.36-1.24 (m, 10H), δ0.88 (t, J=6.6 Hz, 3H)

Production of Organic Transistor and Evaluation of Semiconductor Properties (Mobility)

The production of an organic transistor and evaluation of the semiconductor properties (mobility) were performed in the same manner as in Example 1 except that a compound (2) was used instead of the compound (1). The results are shown in Table 1.

Example 3

Production of Compound (3)

[Chem. 27]

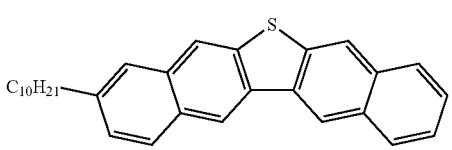

(3)

A compound (3) (yield, 53.2%) in Table was obtained in accordance with Example 1 except that n-hexyl magnesium bromide was changed to n-decyl magnesium bromide in Example 1.

¹H NMR (300 MHz, CDCl₃): δ8.69 (s, 1H), δ8.67 (s, 1H), δ8.21 (s, 1H), δ8.15 (s, 1H), δ8.06-8.03 (m, 1H), δ7.99-7.96 (m, 1H), δ7.92-7.90 (m, 1H), δ7.66 (s, 1H), δ7.54-7.49 (m, 2H), δ7.38 (dd, J=1.5 Hz, 7.8 Hz, 1H), δ2.82 (t, J=7.8 Hz, 2H), δ1.77-1.69 (m, 2H), δ1.42-1.18 (m, 14H), δ0.88 (t, J=6.6 Hz, 3H)

Production of Organic Transistor and Evaluation of Semiconductor Properties (Mobility)

The production of an organic transistor and evaluation of the semiconductor properties (mobility) were performed in the same manner as in Example 1 except that a compound (3) was used instead of the compound (1). The results are shown in Table 1.

Example 4

Production of Compound (4)

[Chem. 28]

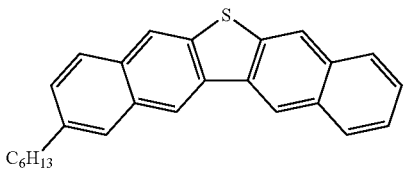

(4)

A compound (4) (yield, 44.6%) was obtained in accordance with Example 1 except that 2-bromo-7-hydroxynaphthalene was changed to 2-bromo-6-hydroxynaphthalene in Example 1.

¹H NMR (300 MHz, CDCl₃): δ8.70 (s, 1H), δ8.66 (s, 1H), δ8.22 (s, 1H), δ8.18 (s, 1H), δ8.07-8.04 (m, 1H), δ7.92-7.90 (m, 1H), δ7.84-7.81 (m, 2H), δ7.56-7.49 (m, 2H), δ7.40 (dd, J=1.7 Hz, 8.3 Hz, 1H), δ2.83 (t, J=7.2 Hz, 2H), δ1.78-1.70 (m, 2H), δ1.42-1.28 (m, 6H), δ0.90 (t, J=6.6 Hz, 3H)

Production of Organic Transistor and Evaluation of Semiconductor Properties (Mobility)

The production of an organic transistor and evaluation of the semiconductor properties (mobility) were performed in the same manner as in Example 1 except that a compound (4) was used instead of the compound (1). The results are shown in Table 1.

Example 5

Production of Compound (5)

[Chem. 29]

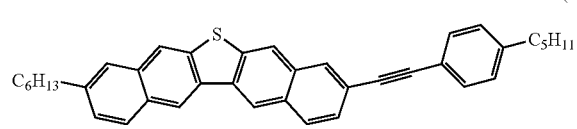

(5)

[Chem. 30]

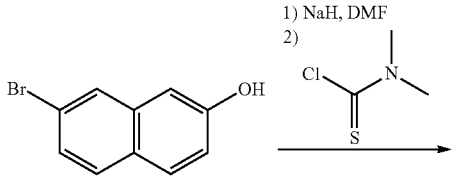

-continued

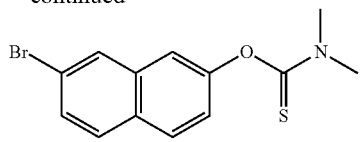

Under the argon atmosphere, 60 mL of dry DMF was added to 15.0 g (67.2 mmol) of 2-bromo-7-hydroxynaphthalene, and the mixture was stirred at 0° C. 9.68 g (202 mmol) of 50% sodium hydride was added to the reaction solution, followed by stirring at room temperature for 30 minutes. 24.9 g (202 mmol) of dimethyl thiocarbamoyl chloride was added to the reaction solution, and the mixture was stirred at 80° C. for 30 minutes. Methanol was added to the reaction solution until bubbling ceased, and then separated and purified by silica gel column chromatography (hexane/ethyl acetate=90/10), and thereby 7.36 g of o-(7-bromonaphthalen-2-yl)-N,N-dimethyl thiocarbamate (yield, 35.3%) was obtained.

$^1$H NMR (300 MHz, CDCl$_3$): δ7.96 (s, 1H), δ7.82 (d, J=8.7 Hz, 1H), δ7.71 (d, J=8.4 Hz, 1H), δ7.53 (dd, J=1.8 Hz, 8.7 Hz, 1H), δ7.41 (d, J=2.4 Hz, 1H), 7.26 (dd, J=2.4 Hz, 9.0 Hz, 1H), δ3.48 (s, 3H), δ3.40 (s, 3H)

[Chem. 31]

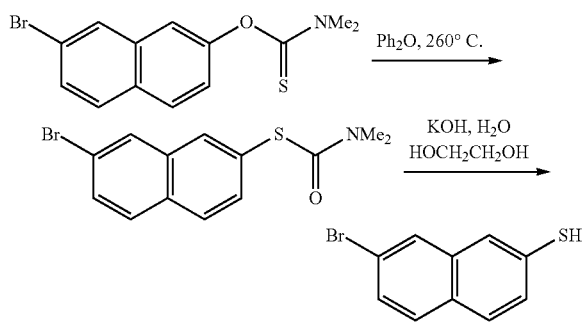

Under the argon atmosphere, 30 mL of diphenyl ether was added to 7.30 g (23.5 mmol) of o-(7-bromonaphthalen-2-yl)-N, N-dimethyl thiocarbamate, and the mixture was heated at 260° C. for 1.5 hours. The reaction mixture was separated by silica gel column chromatography (hexane/ethyl acetate=80/20) so as to obtain 7.4 g of a crude product. Under the argon atmosphere, 300 mL of methanol were added to 7.4 g of the crude product and 11.0 g (195 mmol) of potassium hydroxide, and the mixture was refluxed for three hours. The solvent was distilled off, 300 mL of water was added to the obtained oily liquid, the mixture was cooled to 0° C., concentrated hydrochloric acid was added to the mixture, and the generated white solid was filtered and washed with 500 mL of water. The obtained white solid is dried to thereby obtain 5.22 g of 7-bromo-2-naphthalenethiol (yield, 92.8%).

$^1$H NMR (300 MHz, CDCl$_3$): δ7.84 (m, 1H), δ7.73-7.61 (m, 3H), δ7.45 (dd, J=1.8 Hz, 8.7 Hz, 1H), δ7.33 (dd, J=1.8 Hz, 8.7 Hz, 1H), δ3.62 (s, 1H)

[Chem. 32]

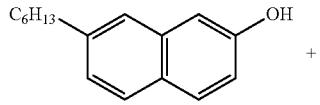

+

-continued

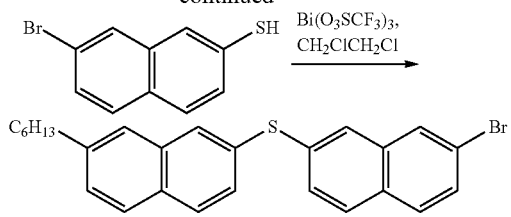

Under the argon atmosphere, 1.7 mL of 1,2-dichloroethane was added to 0.202 g (0.876 mmol) of 2-hexyl-7-hydroxynaphthalene, 0.215 g (0.897 mmol) of 7-bromo-2-naphthalenethiol, and 0.0290 g (0.044 mmol) of bismuth (III) trifluoromethane sulfonate, and the mixture was stirred at 80° C. for 16 hours. The reaction solution was concentrated, and the resultant crude product was separated and purified by silica gel column chromatography (cyclohexane), and thereby 0.306 g of 7-bromo-7'-hexyl-2,2'-binaphthylsulfide (yield, 77.7%) was obtained.

$^1$H NMR (300 MHz, CDCl$_3$): δ7.86 (s, 1H), δ7.82 (d, J=1.8 Hz, 1H), δ7.76-7.61 (m, 5H), δ7.52-7.46 (m, 2H), δ7.40-7.32 (m, 3H), δ2.74 (t, J=7.5 Hz, 2H), δ1.73-1.62 (m, 2H), δ1.41-1.25 (m, 6H), δ0.88 (t, J=6.9 Hz, 3H)

[Chem. 33]

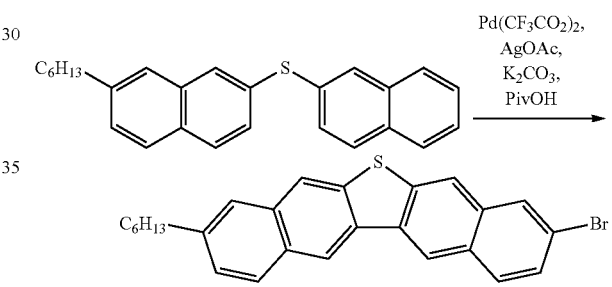

11 mL of pivalic acid was added to 2.40 g (5.34 mmol) of 7-bromo-7'-hexyl-2,2'-binaphthyl sulfide, 0.178 g (0.534 mmol) of palladium (II) trifluoroacetate, 3.57 g (21.4 mmol) silver (I) acetate, and 0.738 g (5.34 mmol) of potassium carbonate, and the mixture was stirred at 110° C. for 16 hours. The reaction solution was diluted with chloroform and filtered through celite. The filtrate was concentrated and the obtained crude product was separated and purified by silica gel column chromatography (hexane), and thereby 0.603 mg of 3-bromo-9-hexyl dinaphtho[2,3-b:2',3'-d]thiophene (yield, 25.2%) was obtained.

$^1$H NMR (300 MHz, CDCl$_3$): δ8.64 (s, 1H), δ8.61 (s, 1H), δ8.13 (s, 1H), δ8.09 (s, 1H), δ8.04 (d, J=1.5 Hz, 1H), δ7.95 (d, J=8.4 Hz, 1H), δ7.89 (d, J=8.7 Hz, 1H), δ7.65 (s, 1H), δ7.56 (dd, J=1.8 Hz, 9.0 Hz, 1H), δ7.38 (dd, J=1.8 Hz, 8.4 Hz, 1H), δ2.81 (t, J=7.5 Hz, 2H), δ1.49-1.68 (m, 2H), δ1.38-1.26 (m, 6H), δ0.90 (t, J=6.9 Hz, 3H)

[Chem. 34]

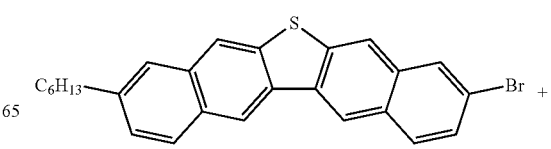

+

-continued

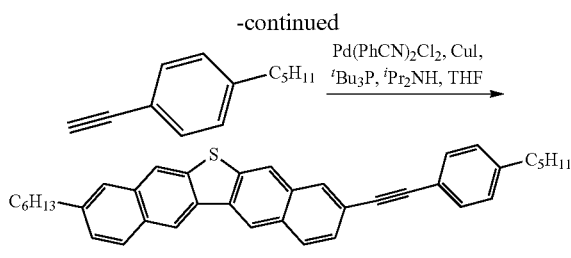

Under the argon atmosphere, 0.22 mL of dry THF, 0.037 mL of diisopropylamine, and 0.019 mL (0.029 mmol) of 1.5M toluene solution of tert-butylphosphine were added to 0.097 g (0.22 mmol) of 3-bromo-9-hexyl dinaphtho[2,3-b:2',3'-d]thiophene, 0.0051 g of dichlorobis (benzonitrile) palladium (II) (0.013 mmol), and 0.0017 g (0.0089 mmol) of copper (I) iodide, and the mixture was stirred at room temperature. 0.046 mL (0.27 mmol) of 1-ethynyl-4-pentylbenzene was added dropwise to the reaction solution, followed by stirring at 60° C. for 8 hours.

350 mL of CHCl$_3$ was added to a reaction solution, and after washing with water, an organic phase was dried with magnesium sulfate and a solvent was distilled off. The obtained crude product is separated and purified by silica gel column chromatography (cyclohexane), and thereby 0.043 mg of 3-hexyl-9-((4-pentylphenyl) ethynyl) dinaphtho[2,3-b:2',3'-d]thiophene (yield, 37%) which is a compound (5) was obtained.

$^1$H NMR (300 MHz, CDCl$_3$): δ8.68 (s, 1H), δ8.65 (s, 1H), δ8.18 (s, 1H), δ8.15 (s, 1H), δ8.09 (s, 1H), δ8.02-7.96 (m, 2H), δ7.67 (s, 1H), δ7.60 (dd, J=1.5 Hz, 8.4 Hz, 1H), δ7.51 (d, J=8.1 Hz, 2H), δ7.39 (dd, J=1.8 Hz, 8.4 Hz, 1H), δ7.20 (d, J=8.1 Hz, 2H), δ2.82 (t, J=7.2 Hz, 2H), δ2.64 (t, J=7.8 Hz, 2H), δ1.77-1.61 (m, 4H), δ1.43-1.27 (m, 10H), δ0.93-0.87 (m, 6H)

Production of Organic Transistor and Evaluation of Semiconductor Properties (Mobility)

The production of an organic transistor and evaluation of the semiconductor properties (mobility) were performed in the same manner as in Example 1 except that a compound (5) was used instead of the compound (1). The results are shown in Table 1.

Example 6

Method of Producing Compound (6)

[Chem. 35]

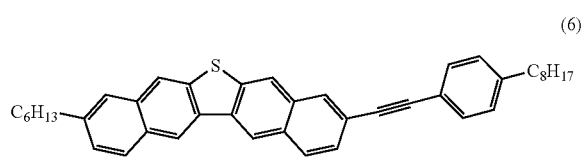

(6)

A compound (6) (yield, 33%) was obtained in accordance with Example 5 except that 1-ethynyl-4-pentylbenzene was changed to 1-ethynyl-4-octylbenzene in Example 5.

$^1$H NMR (300 MHz, CDCl$_3$): δ8.66 (s, 1H), δ8.65 (s, 1H), δ8.17 (s, 1H), δ8.14 (s, 1H), δ8.09 (s, 1H), δ8.01-7.95 (m, 2H), δ7.66 (s, 1H), δ7.61 (dd, J=1.5 Hz, 8.5 Hz, 1H), δ7.51 (d, J=8.1 Hz, 2H), δ7.40 (dd, J=1.8 Hz, 8.5 Hz, 1H), δ7.20 (d, J=8.1 Hz, 2H), δ2.82 (t, J=7.2 Hz, 2H), δ2.64 (t, J=7.8 Hz, 2H), δ1.79-1.58 (m, 4H), δ1.43-1.28 (m, 16H), δ0.92-0.87 (m, 6H).

Production of Organic Transistor and Evaluation of Semiconductor Properties (Mobility)

The production of an organic transistor and evaluation of the semiconductor properties (mobility) were performed in the same manner as in Example 1 except that a compound (6) was used instead of the compound (1). The results are shown in Table 1.

Example 7

Method of Producing Compound (7)

[Chem. 36]

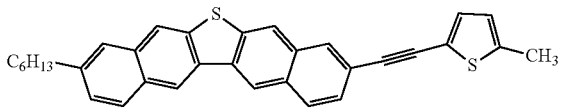

(7)

A compound (7) (yield, 36.8%) was obtained in accordance with Example 5 except that 1-ethynyl-4-pentylbenzene was changed to 2-ethynyl-S-methylthiophene in Example 5.

$^1$H NMR (300 MHz, CDCl$_3$): δ8.66 (s, 1H), δ8.65 (s, 1H), δ8.17 (s, 1H), δ8.14 (s, 1H), δ8.07 (s, 1H), δ8.01-7.96 (m, 2H), δ7.67 (s, 1H), δ7.57 (d, 8.4 Hz, 1H), δ7.39 (d, J=8.4 Hz, 1H), δ7.15 (d, J=2.4 Hz, 1H), δ6.70 (d, J=2.4 Hz, 1H), δ2.82 (t, J=7.5 Hz, 2H), δ2.52 (s, 3H), δ1.76-1.70 (m, 2H), δ1.44-1.28 (m, 6H), δ0.93-0.87 (m, 3H)

Production of Organic Transistor and Evaluation of Semiconductor Properties (Mobility)

The production of an organic transistor and evaluation of the semiconductor properties (mobility) were performed in the same manner as in Example 1 except that a compound (7) was used instead of the compound (1). The results are shown in Table 1.

Comparative Example 1

Method of Producing Compound (179)

A compound represented by General Formula (179) was obtained in accordance with a synthesis method disclosed in WO 2013/125599 Pamphlet.

[Chem. 37]

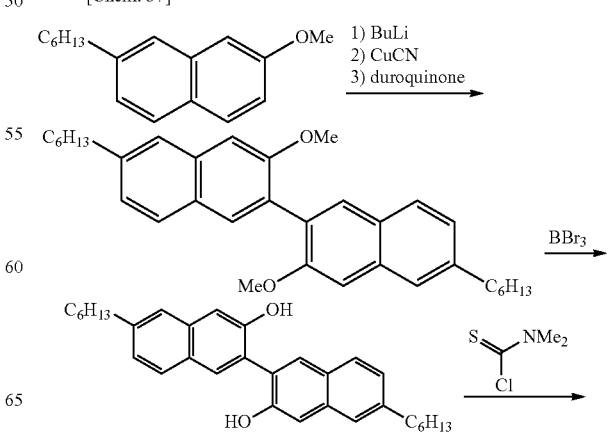

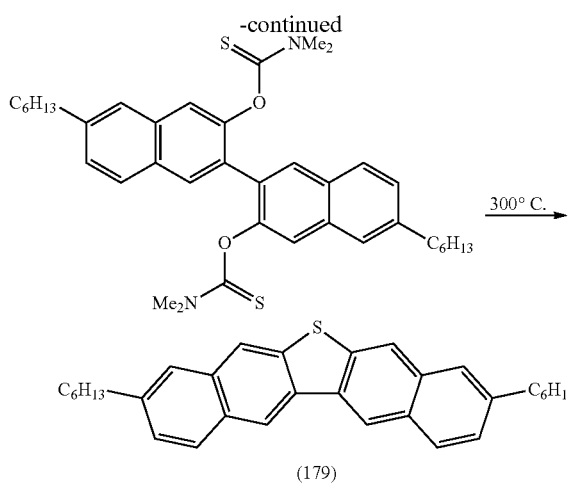

(179)

Production of Organic Transistor and Evaluation of Semiconductor Properties (Mobility)

The production of an organic transistor and evaluation of the semiconductor properties (mobility) were performed in the same manner as in Example 1 except that a compound (179) was used instead of the compound (1). The results are shown in Table 1.

Comparative Example 2

Method of Producing Compound (180)

A compound represented by General Formula (180) was obtained on the basis of Comparative Example 1 except that 2-hexyl-7-methoxynaphthalene was changed to 2-decyl-7-methoxynaphthalene in Comparative Example 1.

[Chem. 38]

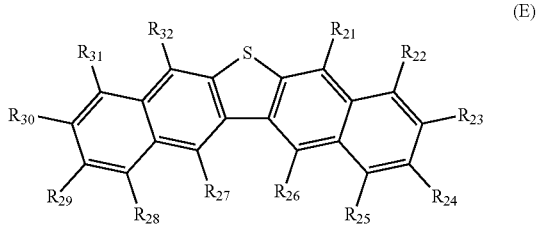

(180)

Production of Organic Transistor and Evaluation of Semiconductor Properties (Mobility)

The production of an organic transistor and evaluation of the semiconductor properties (mobility) were performed in the same manner as in Example 1 except that a compound (180) was used instead of the compound (1). The results are shown in Table 1.

TABLE 1

| Compound | Mobility (cm$^2$/Vs) |
|---|---|
| Example 1 (1) | 2.4 |
| Example 2 (2) | 3.6 |
| Example 3 (3) | 2.7 |
| Example 4 (4) | 1.76 |
| Example 5 (5) | 2.2 |
| Example 6 (6) | 1.6 |
| Example 7 (7) | 3.1 |

TABLE 1-continued

| Compound | Mobility (cm$^2$/Vs) |
|---|---|
| Comparative Example 1 (179) | 0.11 |
| Comparative Example 2 (180) | 0.06 |

As apparent from Table 1, the compound of the present invention is excellent in the solvent solubility and, by using not complicated methods but a simple and practical wet film forming method, that is, only by drop-casting the solution (ink) droplets and then drying them, is capable of forming a transistor having high semiconductor properties (mobility). On the other hand, the compounds indicated in Comparative Examples 1 and 2 which are conventionally well-known compounds cannot exhibit high mobility by such a simple film forming method. As described above, the compound of the present invention has preferable performance in practical use, and it is obvious that the compound of the present invention is superior to the conventionally well-known compound. Accordingly, it is obvious that the preparing method of the present invention which is capable of providing the compound of the present invention is excellent as compared with the conventionally known preparing method.

INDUSTRIAL APPLICABILITY

The compound of the present invention can be used as an organic semiconductor material, and can be used for an organic transistor using the compound of the present invention as organic semiconductor layer.

REFERENCE SIGNS LIST

1: substrate, 2: gate electrode, 3: gate insulating layer, 4: organic semiconductor layer, 5: source electrode, 6: drain electrode

The invention claimed is:
1. A dinaphthothiophene derivative represented by General Formula (E):

[Chem. 1]

(E)

wherein $R_{21}$ to $R_{32}$ each are a hydrogen atom, an acyclic alkyl group having 1 to 20 carbon atoms, Ph-C≡C* wherein Ph represents a phenyl group which may be substituted and * represents a bonding position, or Th-C≡C* wherein Th represents a thienyl group which may be substituted and * represents a bonding position, and wherein $R_{21}$ and $R_{32}$ are the same as or different from each other, $R_{22}$ and $R_{31}$ are the same as or different from each other, $R_{23}$ and $R_{30}$ are the same as or different from each other, $R_{24}$ and $R_{29}$ are the same as or different from each other, $R_{25}$ and $R_{28}$ are the same as or different from each other, and $R_{26}$ and $R_{27}$ are the same as or different from each other provided that, in terms of at least one combination of the six combinations of $R_{21}$ and $R_{32}$, $R_{22}$ and $R_{31}$, $R_{23}$ and $R_{30}$, $R_{24}$ and $R_{29}$, $R_{25}$ and $R_{28}$, and $R_{26}$ and $R_{27}$, the two substituents which constitute the combination are different from each other;

wherein the dinaphthothiophene derivative excludes compounds (E-e) and (E-g):

[Chem. 2]

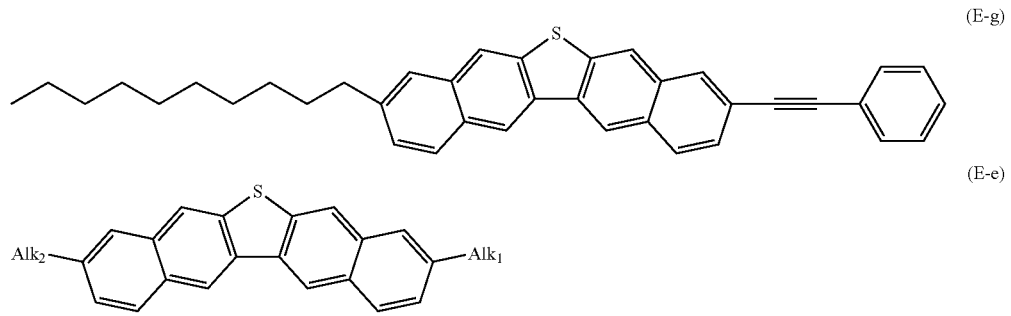

(E-g)

(E-e)

wherein Alk1 and Alk2 represent a linear alkyl group having 1 to 30 carbon atoms.

2. The dinaphthothiophene derivative according to claim 1,
wherein in terms of at least one combination of the six combinations of $R_{21}$ and $R_{32}$, $R_{22}$ and $R_{31}$, $R_{23}$ and $R_{30}$, $R_{24}$ and $R_{29}$, $R_{25}$ and $R_{28}$, and $R_{26}$ and $R_{27}$, the two substituents which constitute the combination are different from each other, and the two substituents which constitute each of the other combinations are the same as each other and are hydrogen atoms.

3. The dinaphthothiophene derivative according to claim 1,
wherein among the six combinations of $R_{21}$ and $R_{32}$, $R_{22}$ and $R_{31}$, $R_{23}$ and $R_{30}$, $R_{24}$ and $R_{29}$, $R_{25}$ and $R_{28}$, and $R_{26}$ and $R_{27}$, the two substituents which constitute each of the combinations of $R_{21}$ and $R_{32}$, $R_{27}$ and $R_{31}$, $R_{25}$ and $R_{28}$, and $R_{26}$ and $R_{27}$ are the same as each other and are hydrogen atoms, $R_{23}$ and $R_{30}$ are the same as or different from each other, $R_{24}$ and $R_{29}$ are the same as or different from each other, and, in terms of at least one combination of two combinations of $R_{23}$ and $R_{30}$, and $R_{24}$ and $R_{29}$, the two substituents which constitute the combination are different from each other.

4. An organic semiconductor material comprising the dinaphthothiophene derivative according to claim 1.

5. An organic semiconductor ink comprising the organic semiconductor material according to claim 4.

6. An organic semiconductor film comprising the organic semiconductor material according to claim 4.

7. An organic semiconductor device comprising the organic semiconductor material according to claim 4.

8. An organic transistor comprising the organic semiconductor material according to claim 4.

9. A preparing method of a dinaphthothiophene derivative according to claim 1, the method comprising the following steps (I) and (II):
(I) a first step of subjecting a naphthol derivative represented by General Formula (A) and a naphthalene thiol derivative represented by General Formula (B) to dehydration condensation in the presence of acid to produce a sulfide derivative represented by General formula (C); and (II) a second step of performing a dehydrogenation reaction of the sulfide derivative (C) in the presence of a transition metal salt or a transition metal complex to produce a dinaphthothiophene derivative according to claim 1.

[Chem. 3]

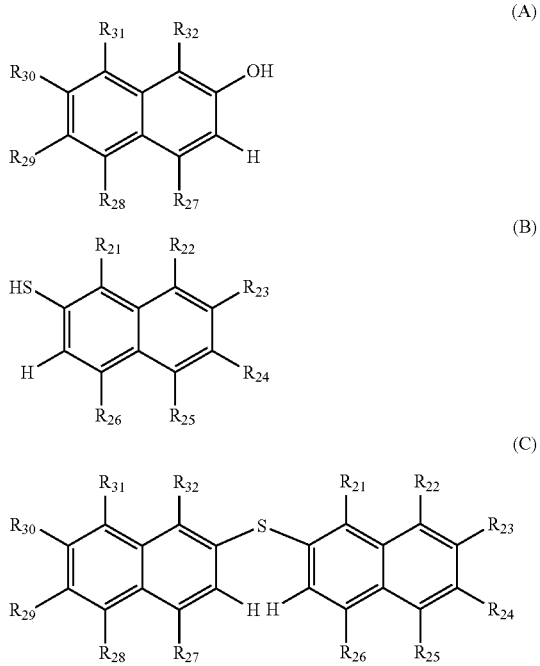

* * * * *